United States Patent
Bolla et al.

(10) Patent No.: US 9,464,032 B2
(45) Date of Patent: Oct. 11, 2016

(54) USE OF POLYAMINOISOPRENYL DERIVATIVES IN ANTIBIOTIC OR ANTISEPTIC TREATMENT

(75) Inventors: Jean-Michel Bolla, Marseilles (FR); Jean Michel Brunel, Marseilles (FR); Joseph Pierre Félix Casanova, Alata (FR); Vannina Lorenzi, Corte (FR); Liliane Berti, Brando (FR)

(73) Assignees: UNIVERSITE D'AIX-MARSEILLE, Marseilles (FR); CENTRE NATIONAL DE LA RECHERCHE SCIENTIFIQUE, Paris (FR); UNIVERSITE DE CORSE, Corte (FR)

( * ) Notice: Subject to any disclaimer, the term of this patent is extended or adjusted under 35 U.S.C. 154(b) by 136 days.

(21) Appl. No.: 14/001,203

(22) PCT Filed: Feb. 23, 2012

(86) PCT No.: PCT/EP2012/053113
§ 371 (c)(1),
(2), (4) Date: Jan. 6, 2014

(87) PCT Pub. No.: WO2012/113891
PCT Pub. Date: Aug. 30, 2012

(65) Prior Publication Data
US 2014/0128335 A1    May 8, 2014

(30) Foreign Application Priority Data
Feb. 23, 2011    (EP) .................................. 11305193

(51) Int. Cl.
| | | |
|---|---|---|
| *A61K 31/32* | (2006.01) | |
| *C07C 211/22* | (2006.01) | |
| *A61K 31/132* | (2006.01) | |
| *A61K 31/16* | (2006.01) | |
| *A61K 31/40* | (2006.01) | |
| *A61K 31/4015* | (2006.01) | |
| *A61K 31/4375* | (2006.01) | |
| *A61K 31/495* | (2006.01) | |
| *A61K 31/5375* | (2006.01) | |
| *A61K 45/06* | (2006.01) | |
| *C07C 211/21* | (2006.01) | |
| *C07C 233/38* | (2006.01) | |
| *C07D 207/27* | (2006.01) | |
| *C07D 295/13* | (2006.01) | |
| *A01N 33/02* | (2006.01) | |
| *A01N 37/18* | (2006.01) | |
(Continued)

(52) U.S. Cl.
CPC ............ *C07C 211/22* (2013.01); *A01N 33/02* (2013.01); *A01N 37/18* (2013.01); *A01N 43/36* (2013.01); *A01N 43/60* (2013.01); *A01N 43/84* (2013.01); *A23L 3/3526* (2013.01); *A61K 8/41* (2013.01); *A61K 8/42* (2013.01); *A61K 8/49* (2013.01); *A61K 8/494* (2013.01); *A61K 8/4913* (2013.01); *A61K 31/131* (2013.01); *A61K 31/132* (2013.01); *A61K 31/16* (2013.01); *A61K 31/165* (2013.01); *A61K 31/40* (2013.01); *A61K 31/4015* (2013.01); *A61K 31/431* (2013.01); *A61K 31/4375* (2013.01); *A61K 31/495* (2013.01); *A61K 31/5375* (2013.01); *A61K 31/546* (2013.01); *A61K 31/65* (2013.01); *A61K 31/7048* (2013.01); *A61K 45/06* (2013.01); *C07C 211/21* (2013.01); *C07C 233/38* (2013.01); *C07D 207/27* (2013.01); *C07D 295/13* (2013.01); *C07D 295/15* (2013.01)

(58) Field of Classification Search
CPC ..................................................... A61K 31/132
USPC .................................................. 560/155, 174
See application file for complete search history.

(56) References Cited

U.S. PATENT DOCUMENTS

| | | | |
|---|---|---|---|
| 3,541,154 | A | 11/1970 | Schmialck et al. |
| 4,762,829 | A | 8/1988 | Yamatsu et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |

FOREIGN PATENT DOCUMENTS

| | | |
|---|---|---|
| EP | 2184061 A1 | 5/2010 |
| JP | 63307849 A | 12/1988 |
| WO | 03/096989 A2 | 11/2003 |

OTHER PUBLICATIONS

Onajole Ok et al; "Synthesis and evaluation of SQ109 analogues as potential anti-tuberculosis candidates", European Journal of Medicinal Chemistry, Editions of Scientifique Elsevier, Paris, FR, vol. 45, No. 5, May 2010, pp. 2075-2079, XP026976532.

(Continued)

*Primary Examiner* — Patrick Lewis
*Assistant Examiner* — Everett White
(74) *Attorney, Agent, or Firm* — Troutman Sanders LLP

(57) ABSTRACT

The present invention relates to the use of polyaminoisoprenyl derivatives in antibiotic or antiseptic treatment of bacteria including those presenting multiple drug resistance (MDR), in particular as efflux pump inhibitors. It also relates to novel polyaminoisoprenyl derivatives, compositions comprising the same, process for preparing the same, and use thereof in antibiotic or antiseptic treatment.

16 Claims, No Drawings

(51) Int. Cl.
*A01N 43/36* (2006.01)
*A01N 43/60* (2006.01)
*A01N 43/84* (2006.01)
*A23L 3/3526* (2006.01)
*A61K 8/41* (2006.01)
*A61K 8/42* (2006.01)
*A61K 8/49* (2006.01)
*A61K 31/131* (2006.01)
*A61K 31/165* (2006.01)
*A61K 31/431* (2006.01)
*A61K 31/546* (2006.01)
*A61K 31/65* (2006.01)
*A61K 31/7048* (2006.01)
*C07D 295/15* (2006.01)

(56) References Cited

OTHER PUBLICATIONS

Oliveira De Am et al; "Structure-activity relationships of 110 candidate juvenile hormone analogs for Panstrongylus megistus (Burmeister, 1835), a vector of Chagas' disease (Hemiptera, Reduviidae, Triatominae)", XP002634547, abstract (1981).

Oliveira De Am et al; "Structure-activity relationships of 110 candidate juvenile hormone analogues for Panstrongylus megistus (Burmeister, 1835), a vector of Chagas disease (Hemiptera, Reduviidae, Triatominae)", Revista Brasileira De Biologia, Sociedad de Biologia de Brasil, Rio de Janeiro, BR, vol. 41, No. 1, 1981, pp. 197-204, XP001001299.

International Search Report and Written Opinion, dated May 18, 2012, which issued during the prosecution of International Patent Application No. PCT/EP2012/053113.

Pradel E and Pagès JM. The AcrAB-TolC efflux pump contributes to multidrug resistance in the noscomial pathogen *Enterobacter aerogenes*. *J. Antimicrob. Chemothe*, Aug. 2002; 46,(8):2640-3.

Chollet R et al. RamA is an alternate activator of the multidrug resistance cascade in *Enterobacter aerogenes*. *J. Antimicrob. Chemother*. Jul. 2004;48,(7):2518-23.

Chollet R et al. The AcrAB-TolC pump is involved in macrolide resistancebut not in telithromycin efflux in *Enterobacter aerogenes* and *Escherichia coli*. J. Antimicrob. Chemother. Sep. 2004;48,(9):3621-4.

Mamelli L et al. Prevalence of efflux activity in low-level macrolide resistant *Campylobacter* species. *J. Antimicrob. Chemother*. Feb. 2007;59,(2):327-8.

Chevalier J et al. Identification and evolution of an efflux pump in clinical *Enterobacter aerogenes* strains isolated in 1995 and 2003. PloS One. Sep. 12, 2008;3(9):e3203.

Lorenzi V et al. Geraniol restores antibiotic activities against multidrug-resistant isolates from gram-negative species. *J. Antimicrob. Chemother*. May 2009;53,(5):2209-11.

Ghisalberti D et al. Chloroquinolines block antibiotic efflux pumps in antibiotic-resistant *Enterobacter aerogenes* isolates. *Int J Antimicrob Agents*. Jun. 2006;27(6):565-9.

Chevalier J et al. Inhibitors of antibiotic efflux in resistant *Enterobacter aerogenes*and *Klebsiella pneumoniae* strains. *J. Antimicrob. Chemother*. Mar. 2004;48,(3):1043-6.

Mallea M et al. Alkylaminoquinolines inhibit the bacterial antibiotic efflux pump in multidrug resistant clinical isolates. *Biochem J*. Dec. 15, 2003;376(Pt 3):801-5.

Baucheron S. et al., AcrAB-TolC directs efflux-mediated multidrug resistance in *Salmonella enterica* serovar Typhymurium DT104. Antimicrob Agents Chemother. 2004 48, 3729-3735.

Dupont M, PagéJM, Lafitte D, Siroy A, Bollet C. Identification of an OprD homologue in Acinetobacter baumannii. J Proteome Res. Nov.-Dec. 2005;4(6):2386- 90.

USE OF POLYAMINOISOPRENYL DERIVATIVES IN ANTIBIOTIC OR ANTISEPTIC TREATMENT

CROSS-REFERENCE TO RELATED APPLICATIONS

This application is a U.S. National Phase application under 35 U.S.C. §371 of International Patent Application No. PCT/EP2012/053113, filed on Feb. 23, 2012, and claims the benefit of European Patent Application No. 11 305 193.2, filed on Feb. 23, 2011, both of which are incorporated herein by reference in their entireties. The International Application published in English on Aug. 30, 2012 as WO 2012/113891 under PCT Article 21(2).

BACKGROUND OF THE INVENTION

Resistance to drugs has implied that efflux mechanisms are processes common to all prokaryotic and eukaryotic cells. It has been responsible for failures in treatment in the battles against cancer, parasites and bacteria. A recent analysis of the situation in Europe conducted by the ECDC (European Centre for Disease Prevention and Control) concluded that there is an increasing gap forming between the number of infections due to multiple drug resistant (MDR) bacteria and the number of cases treatable with new antibiotics. Resistance to antibiotics is increasing in Gram-positive as well as Gram-negative bacteria, which cause serious infections in humans. In the European Union, certain Gram-negative bacteria are becoming more resistant, which has recently been observed in the case of *Escherichia coli*. Every year, approximately 25,000 patients die in the EU (175,000 worldwide) from an infection due to MDR bacteria. Infections due to MDR bacteria induce costs of at least €1.5 billion per year. Currently, production of new agents, targets or mechanisms is lacking for Gram-negative bacteria showing MDR. Therefore, a new strategy has to be put in place in Europe and worldwide to address this problem.

Due to the increasing statistics describing the implication of efflux of antibiotics in inherent (natural) resistance and in the emergence of new MDR bacteria, bacterial efflux pumps have been selected as a possible basis for development of a therapeutic strategy that comprises administration of an antibiotic alongside an efflux inhibitor, restoring thereby its efficiency.

Different strategies are employed to hinder efflux mechanisms. The inhibition of activity of efflux pumps by natural or synthetic compounds represents the state of the art in this approach. These compounds are called "Efflux Pump Inhibitors" (EPI's) and they have the ability to restore the sensitivity of certain bacteria to certain antibiotics. Among these compounds is Phenyl-Arginine β-Naphtylamide (PAβN), which represents the single commercially available active of this type. PAβN is therefore of great importance in the functional study of these mechanisms, which makes up for its lack of clinical application due to its toxicity.

The inventors have significantly helped describe efflux mechanisms of Gram-negative bacteria. They have established model systems, including clinical and genetically modified strains and analytical methods that allow the targeting of compounds capable of inhibiting these mechanisms [1 to 4]. They have identified, on commercial or synthesised molecules, key structures capable of blocking these mechanisms [5 to 10].

In patent application no EP 2,184,061 A1, the inventors disclose the use of geraniol and saturated or unsaturated monoterpene derivatives as bacterial efflux pump inhibitors.

SUMMARY OF THE INVENTION

The inventors have now developed a new class of polyaminoisoprenyl derivatives presenting specific amine groups in various places along the non-terpene side-chain of the molecule, and especially in the terminal position. Such derivatives have tangibly improved or restored antibiotic activity on a variety of Gram-negative bacteria with respect to the prior art.

More particularly, the inventors have shown that the particular new class of polyaminoisoprenyl derivatives significantly reduces MDR of *Enterobacter aerogenes*, *Salmonella enterica* Typhimurium, *Escherichia coli*, *Pseudomonas aeruginosa* and *Acinetobacter baumannii*.

On this basis, polyaminoisoprenyl derivatives of the invention are used as inhibitors of bacterial efflux pumps. Insofar as antibiotics and antiseptics involve efflux pumps, the invention encompasses fighting against bacterial strains, which are naturally antibiotic or antiseptic resistant and/or have developed or are likely to develop antibiotic or antiseptic resistance.

More particularly, the present invention provides polyaminoisoprenyl derivatives for use in the treatment of a subject for reducing antibiotic or antiseptic resistance or restoring antibiotic or antiseptic sensitivity to an antibiotic or antiseptic-resistant bacteria strain.

Advantageously, the polyaminoisoprenyl derivatives of the invention appear to be efficient when administered in association with at least one antibiotic or antiseptic.

The invention finds application in medical, veterinary and non-medical, such as food industry, fields.

DETAILED DESCRIPTION

Accordingly, and in a first aspect of the invention, it is herein disclosed a polyaminoisoprenyl derivative having the following formula (I):

$$A{-}X{-}\underset{\underset{H}{|}}{N}{-}R, \quad (I)$$

wherein

R represents an alkyl group, straight or branched, wherein said alkyl group is interrupted and/or terminated by at least one group selected from N, NH and $NH_2$, X represents a methylene ($CH_2$) group or a carbonyl (C=O) group, and A- represents a group of formula (II):

$$(II)$$

in which n is an integer from 1 to 4 (inclusive), for a use in the treatment of a subject for reducing antibiotic or antiseptic resistance or restoring antibiotic or antiseptic sensitivity to an antibiotic- or antiseptic-resistant bacteria strain.

According to the invention, the term "alkyl" designates a saturated hydrocarbonated group, linear, branched or cyclic (cycloalkyl), having more particularly from 1 to 24, preferably from 2 to 20, more specifically from 5 to 13, carbon atoms, such as methyl, ethyl, propyl, isopropyl, butyl, isobutyl, tert-butyl, pentyl, neopentyl, n-hexyl, heptyl, octyl, nonyl, decyl, dodecyl, undecyl, dodecyl. The alkyl group may be interrupted or terminated by heteroatoms selected from oxygen and sulphur, preferably oxygen atoms.

According to a specific embodiment, R is an alkyl group interrupted and/or terminated by at least one group selected from N, NH and $NH_2$, and also interrupted by at least one oxygen or sulphur atom, more specifically at least one oxygen atom.

As specified above, the alkyl group is interrupted and/or terminated by at least one group selected from N, NH and $NH_2$.

In a particular embodiment, R is an alkyl group terminated by at least one $NH_2$ group.

In another particular embodiment, R is an alkyl group interrupted and/or terminated by at least two groups selected from N, NH and $NH_2$. In a specific embodiment, R may be an alkyl group interrupted by at least one group (for instance one, two or three groups) selected from N and NH, and terminated by at least one (for instance one or two groups) $NH_2$ group.

When R is an alkyl interrupted by at least one N group, the alkyl group can be a cycloalkyl group, such as piperidine or piperazine group, optionally inserted in a linear or branched alkyl chain, forming altogether the R group.

In a particular embodiment, R is an alkyl group, straight or branched, wherein said alkyl group is interrupted and/or terminated by at least one group selected from N, NH and $NH_2$, and wherein at least some of the atoms of R form a cycle.

In particular, at least one N or NH group interrupting or terminating the R alkyl group forms a cycle with other carbon, oxygen and/or sulphur atoms of the R alkyl group.

In particular, the R group may comprise in its alkyl chain, and/or at at least one of its terminations, at least one cycloalkyl group, optionally interrupted by a N or a NH group. Examples of cycloalkyl groups are, but not limited to, piperidine, pyrrolidine, 2-pyrrolidone, and/or piperazine groups. Said cycloalkyl groups may comprise heteroatoms or heterogroups, such as an oxygen atom or a (C=O) group.

n can be 1, 2, 3 or 4. According to a particular embodiment, n is 1 or 2 and more specifically n is 1.

In a particular embodiment, the invention provides novel classes of compounds, such as those of formula (I) where (i) X represents a methylene ($CH_2$) group and/or (ii) n is 1 and/or (iii) R is an alkyl group interrupted and/or terminated by at least two groups selected from N, NH and $NH_2$.

More specifically, the present invention relates to a compound of general formula (I) wherein n is 1 or 2, and R represents an alkyl group, straight or branched, wherein said alkyl group is interrupted and/or terminated by at least two groups selected from N, NH and $NH_2$.

In a particular embodiment, R is an alkyl group terminated by at least one $NH_2$ group (for instance one or two $NH_2$ groups, such as compound 5) and interrupted by at least one group (for instance one, two or three groups) selected from N and NH.

When R is an alkyl interrupted by at least one N group, the alkyl group can be or include a cycloalkyl group, such as piperidine (one N group), pyrrolidine (one N group), morpholine (one N group and one oxygen atom), 2-pyrrolidone (one N group and one C=O group), piperazine (two N groups) group, optionally said cycloalkyl group is inserted in (or at the termination of) a linear or branched alkyl chain, forming altogether the R group.

Examples of compounds comprising a R alkyl group interrupted by at least one N group and including a cycloalkyl group are compounds 2 and 15 (piperazine), compounds 22, 29 and 32 (pyrrolidine), compounds 23, 31 and 34 (morpholine), compounds 30 and 33 (pyrrolidone)

According to the compounds as defined above, n is 1 or 2 and more specifically n is 1.

The compounds of the invention also encompass their stereoisomers (diastereoisomers, enantiomers), pure or mixed, racemic mixtures, geometrical isomers, tautomers, salts, hydrates, solvates, solid forms as well as their mixtures.

This invention concerns "pharmaceutically acceptable" salts of compounds according to the invention. Generally, this term designates slightly- or non-toxic salts obtained from organic or inorganic bases or acids. These salts may be obtained during the final purification step of the compound according to the invention or by incorporating the salt into the purified compound.

Some compounds according to the invention and their salts could be stable in several solid forms. The present invention includes all the solid forms of the compounds according to the invention, which includes amorphous, polymorphous, mono- and polycrystalline forms.

The compounds according to the invention can exist in non-solvated or solvated form, for example with pharmaceutically acceptable solvents such as water (hydrates) or ethanol.

Illustrative compounds particularly useful in the invention are introduced in the Table 1 below.

TABLE 1

Structure

Compound 1: 3,7-Dimethyl-octa-2,6-dienoic acid (2-amino-ethyl)-amide

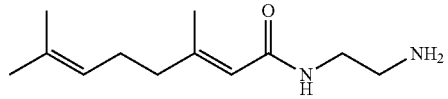

Compound 2: 3,7-Dimethyl-octa-2,6-dienoic acid {3-[4-(3-amino-propyl)-piperazin-1-yl]-propyl}-amide

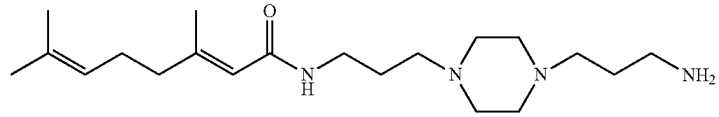 [SMILES: CC(C)=CCC/C(C)=C/C(=O)NCCCN1CCN(CCCN)CC1]

TABLE 1-continued

Structure

Compound 3: 3,7-Dimethyl-octa-2,6-dienoic acid [3-(3-amino-propylamino)-propyl]-amide

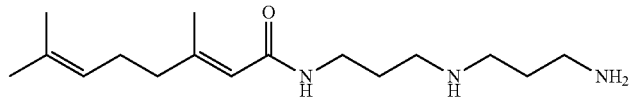 [SMILES: CC(C)=CCC/C(C)=C/C(=O)NCCCNCCCN]

Compound 4: 3,7-Dimethyl-octa-2,6-dienoic acid {2-[2-(2-amino-ethylamino)-ethylamino]-ethyl}-amide

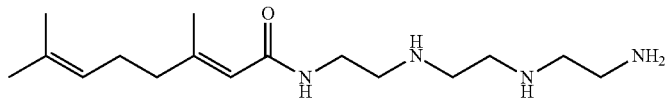 [SMILES: CC(C)=CCC/C(C)=C/C(=O)NCCNCCNCCN]

Compound 5: 3,7-Dimethyl-octa-2,6-dienoic acid {3-[bis-(3-amino-propyl)-amino]-propyl}-amide

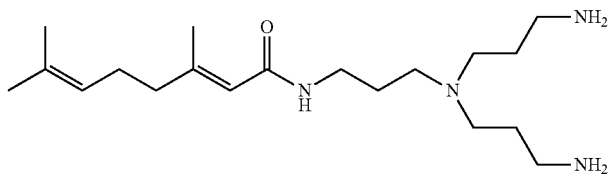 [SMILES: CC(C)=CCC/C(C)=C/C(=O)NCCCN(CCCN)CCCN]

Compound 6: 3,7-Dimethyl-octa-2,6-dienoic acid (12-amino-dodecyl)-amide

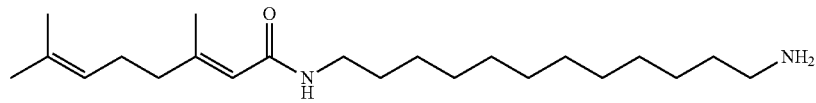 [SMILES: CC(C)=CCC/C(C)=C/C(=O)NCCCCCCCCCCCCN]

Compound 7: 3,7-Dimethyl-octa-2,6-dienoic acid {3-[4-(3-amino-propylamino)-butylamino]-propyl}-amide

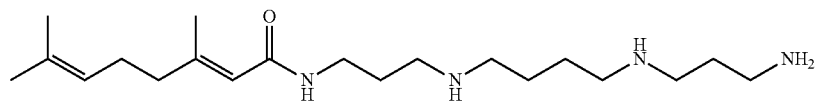 [SMILES: CC(C)=CCC/C(C)=C/C(=O)NCCCNCCCCNCCCN]

Compound 8: {3-[4-(3-Amino-propylamino)-butylamino]-propyl}-(3,7,11-trimethyl-dodeca-2,6,10-trienyl)-amine

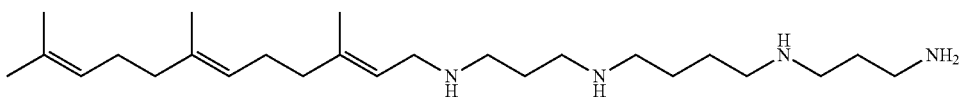 [SMILES: CC(C)=CCC/C(C)=C/CC/C(C)=C/CNCCCNCCCCNCCCN]

Compound 9: {3-[Bis-(3-amino-propyl)-amino]-propyl}-(3,7,11-trimethyl-dodeca-2,6,10-trienyl)-amine

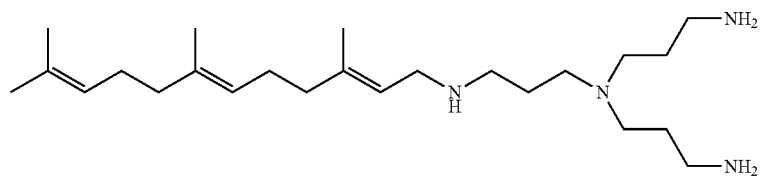 [SMILES: CC(C)=CCC/C(C)=C/CC/C(C)=C/CNCCCN(CCCN)CCCN]

Compound 10: {3-[4-(3-Amino-propylamino)-butylamino]-propyl}-(3,7-dimethyl-octa-2,6-dienyl)-amine

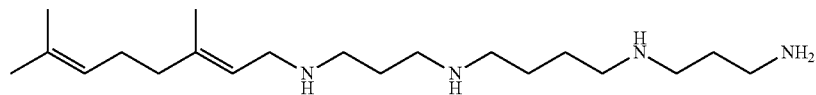 [SMILES: CC(C)=CCC/C(C)=C/CNCCCNCCCCNCCCN]

TABLE 1-continued

Structure

Compound 11: {3-[Bis-(3-amino-propyl)-amino]-propyl}-(3,7-dimethyl-octa-2,6-dienyl)-amine

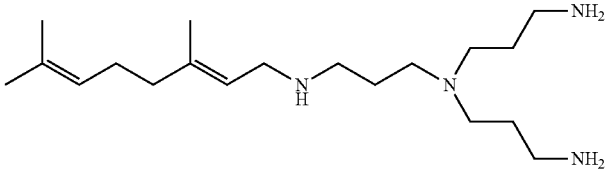 [SMILES: CC(C)=CCC/C(C)=C/CNCCCN(CCCN)CCCN]

Compound 12: (3,7-Dimethyl-octa-2,6-dienyl)-propane-1,3-diamine

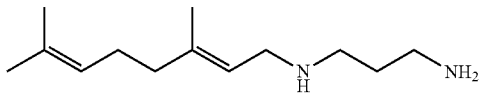

Compound 13: {3-[(3-Amino-propyl)-methyl-amino]-propyl}-((E)-3,7-dimethyl-octa-2,6-dienyl)-amine

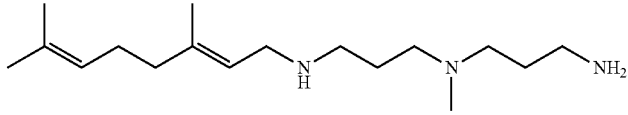 [SMILES: CC(C)=CCC/C(C)=C/CNCCCN(C)CCCN]

Compound 14: {3-[(3-Amino-propyl)-methyl-amino]-propyl}-((2E,6E)-3,7,11-trimethyl-dodeca-2,6,10-trienyl)-amine

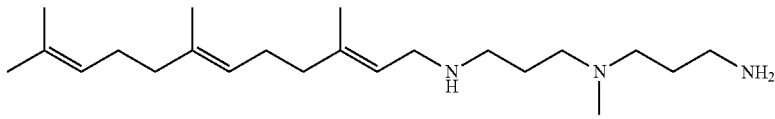 [SMILES: CC(C)=CCC/C(C)=C/CC/C(C)=C/CNCCCN(C)CCCN]

Compound 15: {3-[4-(3-Amino-propyl)-piperazin-1-yl]-propyl}-((2E,6E)-3,7,11-trimethyl-dodeca-2,6,10-trienyl)-amine

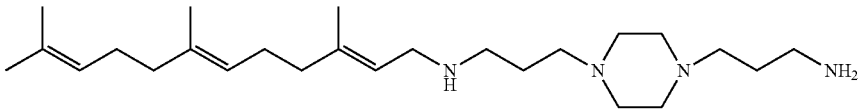 [SMILES: CC(C)=CCC/C(C)=C/CC/C(C)=C/CNCCCN1CCN(CCCN)CC1]

Compound 16: 3,7,11-Trimethyl-dodeca-2,6,10-trienyl)-propane-1,3-diamine

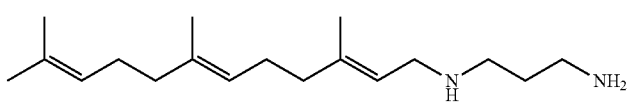 [SMILES: CC(C)=CCC/C(C)=C/CC/C(C)=C/CNCCCN]

Compound 17: 3,7,11-Trimethyl-dodeca-2,6,10-trienyl)-butane-1,4-diamine

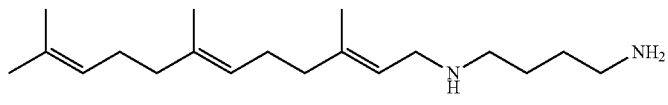 [SMILES: CC(C)=CCC/C(C)=C/CC/C(C)=C/CNCCCCN]

Compound 18: 3,7,11-Trimethyl-dodeca-2,6,10-trienyl)-pentane-1,5-diamine

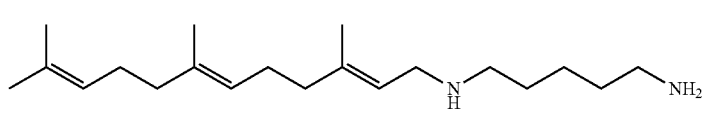 [SMILES: CC(C)=CCC/C(C)=C/CC/C(C)=C/CNCCCCCN]

Compound 19: [3-(4-Amino-butylamino)-propyl]-3,7,11-trimethyl-dodeca-2,6,10-trienyl)-amine

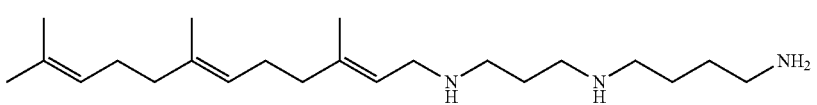 [SMILES: CC(C)=CCC/C(C)=C/CC/C(C)=C/CNCCCNCCCCN]

TABLE 1-continued

Structure

Compound 20: [3-(3-Amino-propylamino)-propyl]-3,7,11-trimethyl-dodeca-2,6,10-trienyl)-amine

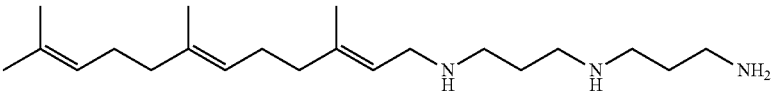 [SMILES: CC(C)=CCC/C(C)=C/CC/C(C)=C/CNCCCNCCCN]

Compound 21: [3-(2-Diethylamino-ethylamino)-propyl]-3,7-dimethyl-octa-2,6-dienyl)-amine

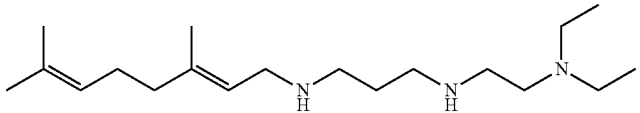 [SMILES: CCN(CC)CCNCCCNC/C=C(\C)CCC=C(C)C]

Compound 22: (3-Pyrrolidin-1-yl-propyl)-3,7,11-trimethyl-dodeca-2,6,10-trienyl)-amine

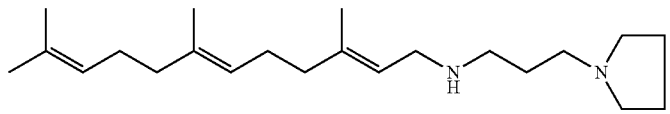 [SMILES: CC(C)=CCC/C(C)=C/CC/C(C)=C/CNCCCN1CCCC1]

Compound 23: (3-Morpholin-4-yl-propyl)-3,7,11-trimethyl-dodeca-2,6,10-trienyl)-amine

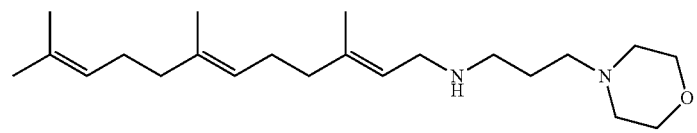 [SMILES: CC(C)=CCC/C(C)=C/CC/C(C)=C/CNCCCN1CCOCC1]

Compound 24: 3,7-Dimethyl-octa-2,6-dienoic acid {3-[3-(3-amino-propoxy)-propoxy]-propyl}-amide

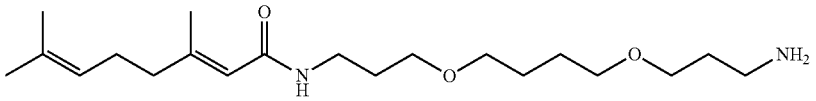 [SMILES: CC(C)=CCC/C(C)=C/C(=O)NCCCOCCCCOCCCN]

Compound 25: [2-(2-{2-[2-(2-Amino-ethylamino)-ethylamino]-ethylamino}-ethylamino)-ethyl]-(3,7-dimethyl-octa-2,6-dienyl)-amine

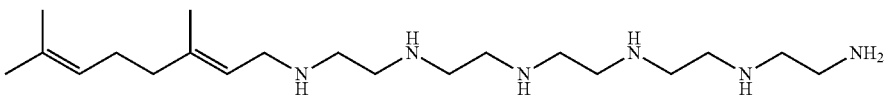 [SMILES: CC(C)=CCC/C(C)=C/CNCCNCCNCCNCCNCCN]

Compound 26: {2-[2-(2-Amino-ethylamino)-ethylamino]-ethyl}-(3,7-dimethyl-octa-2,6-dienyl)-amine

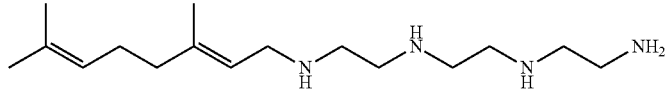 [SMILES: CC(C)=CCC/C(C)=C/CNCCNCCNCCN]

Compound 27: 3,7-Dimethyl-octa-2,6-dienyl)-ethane-1,2-diamine

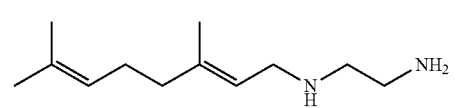

Compound 28: 3,7-Dimethyl-octa-2,6-dienoic acid (3-amino-propyl)-amide

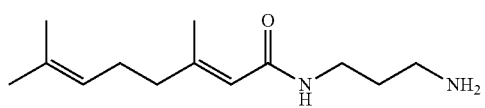 [SMILES: CC(C)=CCC/C(C)=C/C(=O)NCCCN]

TABLE 1-continued

Structure

Compound 29: 3,7-Dimethyl-octa-2,6-dienoic acid (3-pyrrolidin-1-yl-propyl)-amide Compound 30: 3,7-Dimethyl-octa-2,6-dienoic acid [3-(2-oxo-pyrrolidin-1-yl)-propyl]-amide Compound 31: 3,7-Dimethyl-octa-2,6-dienoic acid (3-morpholin-4-yl-propyl)-amide Compound 32: 3,7-Dimethyl-octa-2,6-dienyl)-(3-pyrrolidin-1-yl-propyl)-amine Compound 33: 1-[3-(3,7-Dimethyl-octa-2,6-dienylamino)-propyl]-pyrrolidin-2-one Compound 34: 3,7-Dimethyl-octa-2,6-dienyl-(3-morpholin-4-yl-propyl)-amine Compound 35: [2-(2-{2-[2-(2-Amino-ethylamino)-ethylamino)-ethylamino}-ethylamino)-ethyl]-(3,7,11-trimethyl-dodeca-2,6,10-trienyl)-amine Compound 36: (2-{2-[2-(2-Amino-ethylamino)-ethylamino]-ethylamino}-ethyl)-(3,7,11-trimethyl-dodeca-2,6,10-trienyl)-amine TABLE 1-continued Structure Compound 37: 3,7,11-Trimethyl-dodeca-2,6,10-trienyl-ethane-1,2-diamine Compound 38: 3,7,11-Trimethyl-dodeca-2,6,10-trienyl-dodecane-1,12-diamine Compound 39: N,N-Diethyl-N-(3,7,11-trimethyl-dodeca-2,6,10-trienyl)-hexane-1,5-diamine Compound 40: {3-[3-(3-Amino-propoxy)-propoxy]-propyl}-(3,7,11-trimethyl-dodeca-2,6,10-trienyl)-amine In some embodiments, the compounds of the invention are selected from compounds 1 to 23, 35 and 36.

In some preferred embodiments, the compounds of the invention are selected from compounds 5, 7, 8, 9, 10, 11, 12, 13, 14, 15, 16, 17, 18, 19, 20, 21, 22, and 23.

In an embodiment, the compounds of the invention are selected in the group consisting of:

3,7-Dimethyl-octa-2,6-dienoic acid {3-[4-(3-amino-propyl)-piperazin-1-yl]-propyl}-amide (compound 2), 3,7-Dimethyl-octa-2,6-dienoic acid [3-(3-amino-propylamino)-propyl]-amide (compound 3), 3,7-Dimethyl-octa-2,6-dienoic acid {2-[2-(2-amino-ethylamino)-ethylamino]-ethyl}-amide (compound 4), 3,7-Dimethyl-octa-2,6-dienoic acid {3-[bis-(3-amino-propyl)-amino]-propyl}-amide (compound 5), 3,7-Dimethyl-octa-2,6-dienoic acid {3-[4-(3-amino-propylamino)-butylamino]-propyl}-amide (compound 7), {3-[4-(3-Amino-propylamino)-butylamino]-propyl}-(3,7,11-trimethyl-dodeca-2,6,10-trienyl)-amine (compound 8), {3-[Bis-(3-amino-propyl)-amino]-propyl}-(3,7,11-trimethyl-dodeca-2,6,10-trienyl)-amine (compound 9), {3-[4-(3-Amino-propylamino)-butylamino]-propyl}-(3,7-dimethyl-octa-2,6-dienyl)-amine (compound 10), {3-[Bis-(3-amino-propyl)-amino]-propyl}-(3,7-dimethyl-octa-2,6-dienyl)-amine (compound 11), {3-[(3-Amino-propyl)-methyl-amino]-propyl}-((E)-3,7-dimethyl-octa-2,6-dienyl)-amine (compound 13), {3-[(3-Amino-propyl)-methyl-amino]-propyl}-((2E,6E)-3,7,11-trimethyl-dodeca-2,6,10-trienyl)-amine (compound 14), {3-[4-(3-Amino-propyl)-piperazin-1-yl]-propyl}-((2E,6E)-3,7,11-trimethyl-dodeca-2,6,10-trienyl)-amine (compound 15),

[3-(4-Amino-butylamino)-propyl]-3,7,11-trimethyl-dodeca-2,6,10-trienyl)-amine (compound 19),

[3-(3-Amino-propylamino)-propyl]-3,7,11-trimethyl-dodeca-2,6,10-trienyl)-amine (compound 20),

[3-(2-Diethylamino-ethylamino)-propyl]-3,7-dimethyl-octa-2,6-dienyl)-amine (compound 21),

[2-(2-{2-[2-(2-Amino-ethylamino)-ethylamino]-ethylamino}-ethylamino)-ethyl]-(3,7-dimethyl-octa-2,6-dienyl)-amine (compound 25), {2-[2-(2-Amino-ethylamino)-ethylamino]-ethyl}-(3,7-dimethyl-octa-2,6-dienyl)-amine (compound 26),

[2-(2-{2-[2-(2-Amino-ethylamino)-ethylamino]-ethylamino}-ethylamino)-ethyl]-(3,7,11-trimethyl-dodeca-2,6,10-trienyl)-amine (compound 35), and (2-{2-[2-(2-Amino-ethylamino)-ethylamino]-ethylamino}-ethyl)-(3,7,11-trimethyl-dodeca-2,6,10-trienyl)-amine (compound 36).

In an embodiment, the compounds of the invention are selected in the group consisting of (3,7-Dimethyl-octa-2,6-dienyl)-propane-1,3-diamine (compound 12), 3,7,11-Trimethyl-dodeca-2,6,10-trienyl)-propane-1,3-diamine (compound 16), 3,7,11-Trimethyl-dodeca-2,6,10-trienyl)-butane-1,4-diamine (compound 17), 3,7,11-Trimethyl-dodeca-2,6,10-trienyl)-pentane-1,5-diamine (compound 18), (3-Pyrrolidin-1-yl-propyl)-3,7,11-trimethyl-dodeca-2,6,10-trienyl)-amine (compound 22), (3-Morpholin-4-yl-propyl)-3,7,11-trimethyl-dodeca-2,6,10-trienyl)-amine (compound 23), 3,7-Dimethyl-octa-2,6-dienoic acid {3-[3-(3-amino-propoxy)-propoxy]-propyl}-amide (compound 24), {3-[3-(3-Amino-propoxy)-propoxy]-propyl}-(3,7,11-trimethyl-dodeca-2,6,10-trienyl)-amine (compound 40), 3,7-Dimethyl-octa-2,6-dienoic acid (3-amino-propyl)-amide (compound 28),
3,7-Dimethyl-octa-2,6-dienoic acid (3-pyrrolidin-1-yl-propyl)-amide (compound 29),
3,7-Dimethyl-octa-2,6-dienoic acid [3-(2-oxo-pyrrolidin-1-yl)-propyl]-amide (compound 30),
3,7-Dimethyl-octa-2,6-dienoic acid (3-morpholin-4-yl-propyl)-amide (compound 31),
3,7-Dimethyl-octa-2,6-dienyl)-(3-pyrrolidin-1-yl-propyl)-amine (compound 32),
1-[3-(3,7-Dimethyl-octa-2,6-dienylamino)-propyl]-pyrrolidin-2-one (compound 33),
3,7-Dimethyl-octa-2,6-dienyl-(3-morpholin-4-yl-propyl)-amine (compound 34),
3,7,11-Trimethyl-dodeca-2,6,10-trienyl-dodecane-1,12-diamine (compound 38), and
N,N-Diethyl-N-(3,7,11-trimethyl-dodeca-2,6,10-trienyl)-hexane-1,5-diamine (compound 39).

The compounds according to the present invention may be prepared by various methods known to those skilled in the art. More preferably, several chemical routes have been carried out. The present invention also concerns a process for preparing the compounds of the invention.

Concerning the derivatives issued from geranic acid the reaction involved a BOP peptide coupling reaction as illustrated in Scheme 1. This reaction proceeds at room temperature preferentially in dichloromethane, but it can also be conducted in other solvents, such as chloroform, THF, or toluene, in a range of temperature around 0-100° C. and using 1 equivalent of Benzotriazol-1-yloxy)tris(dimethylamino)phosphonium hexafluorophosphate (BOP) and 1 equivalent of Diisopropylethylamine.

Scheme 1

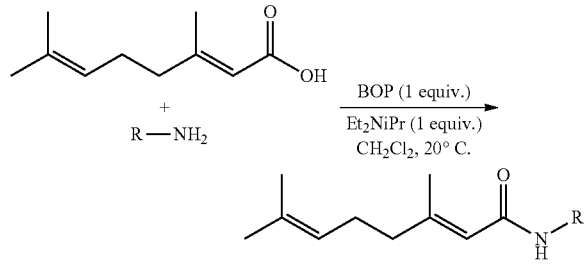

R in scheme 1 is as defined above for formulae (I).

Concerning derivatives issued from citral or farnesal starting materials, the reaction involved is a titanium reductive amination proceeding typically in methanol at room temperature (see Scheme 2), but it can also be conducted in other solvents, such as chloroform, THF, toluene, in a range of temperature around 0-100° C. and using 1 equivalent of titanium isopropoxide.

Scheme 2

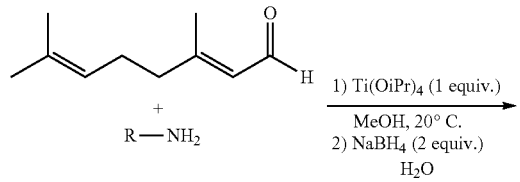

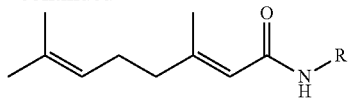

R in scheme 2 is as defined above for formulae (I).

According to the present invention, the polyaminoisoprenyl derivatives of the invention are useful for weakening the resistance of gram-negative bacteria to an antibiotic or antiseptic, or for the full restoration of activity of an antibiotic or antiseptic with respect to a species of gram-negative bacteria.

In a preferred embodiment, polyaminoisoprenyl derivatives are for use in treating a subject infected with an antibiotic- or an antiseptic-resistant bacteria strain.

The subject may be any animal likely to be infected with such strains, preferably a human being or a mammal, including cattle, sheep, horses, dogs, cats, goats etc. Poultry, fish or any other animals for food industry are also encompassed. Preferably the subject is a human patient, whatever its age or sex. New-borns, infants, children are included as well.

Accordingly, it is herein disclosed a method for reducing antibiotic or antiseptic resistance or restoring antibiotic or antiseptic sensitivity to an antibiotic or antiseptic-resistant bacteria strain in a subject infected with such strain, which method comprises administering to said subject an effective amount of at least one of polyaminoisoprenyl derivatives of the invention.

In a particular embodiment, polyaminoisoprenyl derivatives are intended for use in local treatment of wounds infected with antiseptic or antibiotic resistant bacterial strains.

According to the present invention, polyaminoisoprenyl derivatives are useful in reducing resistance or restoring sensitivity to any antibiotic or antiseptic-resistant bacteria, including Gram-negative bacteria or Gram-positive bacteria.

In a preferred embodiment, the bacteria strain is a Gram-negative bacteria strain.

The proteobacteria are a major group of Gram-negative bacteria, including *Escherichia coli, Salmonella*, and other Enterobacteriaceae, *Pseudomonas, Acinetobacter, Moraxella, Helicobacter, Stenotrophomonas, Bdellovibrio*, acetic acid bacteria, *Legionella* and alpha-proteobacteria as *Wolbachia* and many others. Other notable groups of Gram-negative bacteria include the cyanobacteria, spirochaetes, green sulfur and green non-sulfur bacteria. Medically relevant Gram-negative cocci include three organisms, which cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Proteus mirabilis, Providencia stuartii, Klebsiella pneumoniae, Enterobacter cloacae and aerogenes, Serratia marcescens*), and primarily gastrointestinal problems (*Campylobacter, Helicobacter pylori, Salmonella enteritidis*, Enteropathogenic *Escherichia coli, Salmonella typhi*).

Gram-negative bacteria associated with nosocomial infections include *Escherichia coli, Pseudomonas*, or *Acinetobacter baumanii*, which cause bacteremia, secondary meningitis, and ventilator-associated pneumonia in intensive care units of hospital establishments.

Gram-negative bacteria considered as potential weapons include *Burkholderia cepacia, Burkholderia thalandensis, Burkholderia mallei, Burkholderia pseudomallei, Francisella tularensis*, or *Yersinia pestis*.

Polyaminoisoprenyl derivatives of the invention are particularly useful in reducing antibiotic resistance or restoring antibiotic sensitivity in at least one of the above-mentioned Gram-negative bacteria.

In a preferred embodiment, polyaminoisoprenyl derivatives are intended for use in a subject infected with enteropathogenic or uropathogenic bacterial strains. More specifically, the patient is infected with *Enterobacter* (in particular *Enterobacter aerogenes*), *Escherichia coli, Pseudomonas* (in particular *Pseudomonas aeruginosa*) and *Acinetobacter* (in particular *Acinetobacter baumannii*), *Klebsellia, Salmonella, Burkholderia, Campylobacter* or *Helicobacter* species.

Preferably the patient is infected with MDR strains of the above bacteria.

The mechanism behind MDR of pathogenic Gram-negative bacteria is now accepted to be due to over-expressed efflux pumps that extrude a large number of unrelated antibiotics and antiseptics prior to reaching their intended targets. Gram-negative bacteria contain a large number of efflux pumps, which, at face value, appear, to be redundant. Compounds of the invention are more particularly used in accordance with the invention as inhibitors of bacterial efflux pumps.

Polyaminoisoprenyl derivatives are preferably applied or administered in combination with an antibiotic or an antiseptic, the effect of which is increased by the action of polyaminoisoprenyl derivatives of the invention.

Compounds according to the invention are particularly useful in combination with an antibiotic or an antiseptic. Accordingly, the compounds of the invention are used in combination with an antibiotic or an antiseptic to treat a subject infected with a bacterial strain.

The term "combination" or "association" means that polyaminoisoprenyl derivatives are applied or administered simultaneously or sequentially with the antibiotic or antiseptic. In the context of a medical treatment, polyaminoisoprenyl derivatives of the invention, and the antibiotic or antiseptic are administered preferably the same day, most preferably within an interval of 2 hours, preferably 1 hour, at most.

As stated above, polyaminoisoprenyl derivatives are preferably applied or administered in combination with an antibiotic or an antiseptic, the effect of which is increased by the action of polyaminoisoprenyl derivatives of the invention. In particular, polyaminoisoprenyl derivatives are very useful since they appear to be efficient with one or more antibiotics or antiseptics against one or more bacteria strains.

Examples of antibiotics include beta-lactam antibiotics (such as oxacillin), macrolides (such as erythromycin, clarithromycin, tylosin, spyramycin and azitromycin), ketolides (such as telithromycin), monobactams, penicillins, cephalosporins (such as cefepime), carbapenems, aminosides (such as gentamycin), rifamycins, tetracycline antibiotics (such as doxycycline and tetracycline), chloramphenicol, clindamycin, lincomycin, fusidic acid, novobiocin, fosfomycin, fusidate sodium, capreomycin, colistimethate, gramicidin, minocycline, doxycycline, tigecycline, bacitracin, quinolones (such as nalidixic acid), fluoroquinolones (such as ciprofloxacin), glycopeptides (such as vancomycin), trimethoprim, or sulfamides (such as sulfomthoxazole).

In the context of the present invention, the term "antiseptics" refers to antibacterial agents, including bacteriocidal or bacteriostatic agents. Antiseptics include ethanol, isopropanol, glutaraldehyde, tricocarban, chlorhexidine, alexidine, polymeric biguanides, triclosan, hexachlorophene, propamidine, dibromopropamidine, chloroxylenol, chlorine or iodine releasing compounds, silver or mercury compounds, hydrogen peroxide, ozone, peracetic acid, phenol, cresol, cetrimide, benzalkonium chloride, ethylene oxide, formaldehyde, benzoic acid, or quaternary ammoniums.

In some embodiments, the antibiotic is selected from the group consisting of beta-lactam antibiotics, quinolone antibiotics, tetracycline antibiotics, macrolide antibiotics, chloramphenicol, cephalosporin antibiotics and combinations thereof.

In some other embodiments, the antibiotic is selected from the group consisting of chloramphenicol, nalidixic acid, macrolides (such as erythromycin, clarithromycin, tylosin, spyramycin and azitromycin), tetracycline antibiotics (such as doxycycline and tetracycline) and combinations thereof. In some additional embodiments, the compounds of the invention are used in the treatment of a subject for reducing antibiotic or antiseptic resistance or restoring antibiotic or antiseptic sensitivity to an antibiotic- or antiseptic-resistant bacteria strain, wherein:

The antibiotic is selected from an antibiotic selected from the group consisting of beta-lactam antibiotics, quinolone antibiotics, tetracycline antibiotics, macrolide antibiotics, chloramphenicol, cephalosporin antibiotics and combinations thereof and, The bacterial strain is selected from the group consisting of *Escherichia coli, Pseudomonas, Acinetobacter, Salmonella, Enterobacter* strains and combination thereof.

As mentioned previously, the compounds of the invention may be selected from the group consisting of compounds 1 to 23, 35 and 36, preferably from compounds 5, 7, 8, 9, 10, 11, 12, 13, 14, 15, 16, 17, 18, 19, 20, 21, 22, and 23.

As illustrated in the examples, the compounds of the invention may be used for reducing the inherent resistance of a gram-negative bacterial strain to macrolide antibiotics.

Accordingly, in some specific embodiments, the compounds of the invention are used in the treatment of a subject for reducing resistance to a macrolide in a gram-negative bacterial strain. Appropriate compounds include, without being limited to, compounds 3, 4, 7, 5, 10, 11, 14, 15 and 35.

In the context of a medical or veterinary treatment, polyaminoisoprenyl derivatives of the invention may be administered to a subject by any suitable route, including oral, topical, sublingual, parenteral (preferably intravenous), transdermal, rectal, etc.

For a brief review of present methods for drug delivery, see, Langer, Science 249:1527-1533 (1990), which is incorporated herein by reference.

Topical administration on wounds may be particularly advantageous against *Pseudomonas* infections, for instance. Otherwise, oral administration may be particularly convenient.

In the veterinary field, topical administration, e.g. treatment of wounds, may be advantageous too.

In agricultural and food industry, a treatment of animals in slaughterhouse may be contemplated, e.g. by spraying or dipping the animal, e.g. poultry, or parts thereof, in washing baths.

The present invention also concerns a pharmaceutical composition comprising a compound of the invention, in particular a compound of formula (I), as described above, and a pharmaceutically acceptable carrier and/or excipient. This particular aspect also concerns the preferred embodiments disclosed above for the compounds of the invention. In a particular embodiment, the pharmaceutical composition comprises a compound according to any of the above defined embodiments.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. As stated earlier, possible pharmaceutical compositions include those suitable for oral, rectal, topical, transdermal, buccal, sublingual, or parenteral (including subcutaneous, intramuscular, intravenous and intradermal) administration. For these formulations, conventional excipients can be used according to techniques well known by those skilled in the art. The compositions for parenteral administration are generally physiologically compatible sterile solutions or suspensions which can optionally be prepared immediately before use from solid or lyophilized form. For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents, which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. For transdermal administration, the composition can be formulated into ointment, cream or gel form and appropriate penetrants or detergents could be used to facilitate permeation, such as dimethyl sulfoxide, dimethyl acetamide and dimethylformamide. For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. In a preferred embodiment, the pharmaceutical composition of the invention is suitable for parenteral administration.

Pharmaceutical composition according to the invention may be formulated to release the active drug substantially immediately upon administration or at any predetermined time or a time period after administration.

In a particular embodiment, the pharmaceutical composition according to the invention comprises 0.001 mg to 1 g of the compound of the invention. Preferably, pharmaceutical composition according to the invention comprises 0.01 mg to 800 mg of the compound of the invention.

Pharmaceutical compositions according to the invention can comprise one or more compound of the invention in association with pharmaceutically acceptable excipients and/or carriers. These excipients and/or carriers are chosen according to the form of administration as described above.

As stated above, compounds of the invention are more particularly useful in combination with an antibiotic or an antiseptic. The present invention also relates to a pharmaceutical composition comprising at least one compound of the present invention and an antibiotic or an antiseptic. The present invention also concerns a product containing a compound of the present invention and an antibiotic or an antiseptic, as a combined preparation for simultaneous, separate or sequential use, in particular for a treatment of bacterial infection.

Compounds according to the invention are particularly combined with an antibiotic selected from the group consisting of beta-lactam antibiotics, macrolides, ketolides, monobactams, penicillins, cephalosporins, carbapenems, aminosides, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, tigecycline, bacitracin, quinolones, fluoroquinolones, glycopeptides, trimethoprim and sulfamides.

In another embodiment, polyaminoisoprenyl derivatives of the invention are for use in vitro in disinfecting a product (i.e. a non-living product) infected (or contaminated), or likely to be infected, with an antibiotic- or an antiseptic-resistant bacteria strain. In a particular embodiment, the product may also be a medical device. In another particular embodiment, the product may be a food product, e.g. a dairy or meat product, or a drink.

In another embodiment, polyaminoisoprenyl derivatives are for use in preserving a product or preventing infection of a product, preferably in association with preservatives. In a particular embodiment, the product may be a cosmetic product or composition.

Accordingly, it is herein disclosed an in vitro and/or ex vivo method for reducing antibiotic or antiseptic resistance or restoring antibiotic or antiseptic sensitivity to an antibiotic or antiseptic-resistant bacteria strain in a product infected or likely to be infected with such strain, which method comprises contacting said product with an effective amount of at least one of polyaminoisoprenyl derivative of the invention.

When used for disinfecting a product, polyaminoisoprenyl derivatives of the invention may be e.g. in form of a solution applied to the surface of the product, or a bath into which the product is dipped.

Moreover, the invention relates to a compound according to the invention for use in the prevention and/or the treatment of an infectious disease in a subject, preferably in combination with an antibiotic.

Further objects of the invention are methods corresponding to the uses of the compounds of the invention which are described above.

For instance, a further object of the invention relates to a method for disinfecting a product infected, or likely to be infected, with an antibiotic- or an antiseptic-resistant bacterial strain, the said method comprising the step of contacting the product with a compound according to the invention, optionally in combination with an antiseptic or an antibiotic.

The present invention also relates to a method for treating a patient who is infected or may be infected by an antibiotic- or antiseptic-resistant bacterial strain, the said method comprises the step of administering to the said patient a compound according to the invention, preferably in an amount effective for reducing antibiotic or antiseptic resistance or for restoring antibiotic or antiseptic sensitivity to the said bacterial strain.

An additional object of the invention is a method for treating and/or preventing an infectious (bacterial) disease in a patient comprising the step of administering to the said patient an effective amount of a compound according to the invention, preferably in combination with an antibiotic.

As mentioned above, the antibiotic and the compound of the invention may be administered simultaneously or sequentially.

The below Examples illustrate the invention without reducing its scope.

EXAMPLES

Example 1

General Procedure for the Synthesis of the Compounds 1-7 According to the Invention The general synthetic pathway for the preparation of polyaminoisoprenyl derivatives 1-7 of the invention can be illustrated by the example below which represents the preparation of compound 7 (yield: 75% by weight).

$NH_4OH$ (7/3/1) eluent affording the expected coupling product 7 in 75% yield.

Compound 7, Yellow solid; $^1$H NMR (MeOD): δ=5.49-5.21 (m, 2H), 3.51 (m, 2H), 2.71-2.03 (m, 24H), 1.74-1.61 (m, 12H). $^{13}$C (MeOD): δ=170.41, 153.39, 133.58, 124.96, 119.62, 56.40, 54.04, 50.56, 47.96, 45.92, 42.21, 38.00, 30.22, 28.33, 27.68, 26.36, 25.69, 19.02, 18.25. $C_{20}H_{40}N_4O$ m/z 353.3275 (100%, (M+H$^+$))

Compound 1, Yellow solid; $^1$H NMR (MeOD): δ=5.48-5.15 (m, 2H), 4.22-3.52 (m, 5H), 2.87-2.06 (m, 9H), 1.62 (m, 6H). $^{13}$C (MeOD): δ=164.88, 151.58, 132.75, 123.30, 118.63, 43.53, 42.68, 40.12, 25.95, 25.53, 20.38, 17.66. $C_{12}H_{22}N_2O$ m/z 211.1805 (100%, (M+H$^+$)).

Compound 2, Yellow solid; $^1$H NMR (MeOD): δ=5.53-5.21 (m, 2H), 3.39-3.09 (m, 5H), 2.81-2.06 (m, 21H), 1.73-1.28 (m, 8H). $^{13}$C (MeOD): δ=164.88, 151.58, 132.75, 123.30, 118.93, 51.86, 51.56, 51.35, 51.01, 40.30, 35.65, 30.71, 25.95, 25.56, 19.33, 17.63. $C_{20}H_{38}N_4O$ m/z 351.3118 (100%, (M+H$^+$))

Compound 3, Yellow solid; $^1$H NMR (MeOD): δ=5.49-5.16 (m, 2H), 3.51 (m, 2H), 2.73-2.06 (m, 19H), 1.64-1.61 (m, 8H). $^{13}$C (MeOD): δ=170.07, 151.58, 132.75, 123.30, 119.42, 52.13, 47.23, 40.60, 36.13, 33.53, 26.02, 25.76, 19.32, 17.20. $C_{16}H_{31}N_3O$ m/z 282.2540 (100%, (M+H$^+$))

Compound 4, Yellow solid; $^1$H NMR (MeOD): δ=5.46-5.17 (m, 2H), 3.49 (m, 2H), 2.73-2.05 (m, 22H), 1.63-1.60 (m, 6H). $^{13}$C (MeOD): δ=168.48, 151.63, 132.32, 123.30, 118.29, 51.61, 51.30, 48.14, 41.12, 40.23, 25.95, 20.35, 17.63. $C_{16}H_{32}N_4O$ m/z 297.2649 (100%, (M+H$^+$))

Compound 5, Yellow solid; $^1$H NMR (MeOD): δ=5.49-5.16 (m, 2H), 3.51 (m, 2H), 2.64-2.36 (m, 15H), 2.20-1.63 (m, 13H), 1.49-1.38 (m, 6H). $^{13}$C (MeOD): δ=170.07, 151.58, 132.75, 123.30, 119.32, 51.67, 40.30, 36.73, 31.02, 26.52, 25.57, 20.35, 17.30.

Compound 6, Yellow solid; $^1$H NMR (MeOD): δ=5.49-5.07 (m, 2H), 3.25-3.12 (m, 5H), 2.74-2.06 (m, 14H), 1.71-1.21 (m, 26H). $^{13}$C (MeOD): δ=169.30, 152.14, 132.75, 123.18, 118.92, 42.61, 40.44, 39.33, 34.61, 29.38, 29.31, 28.83, 27.40, 25.95, 21.12, 17.34.

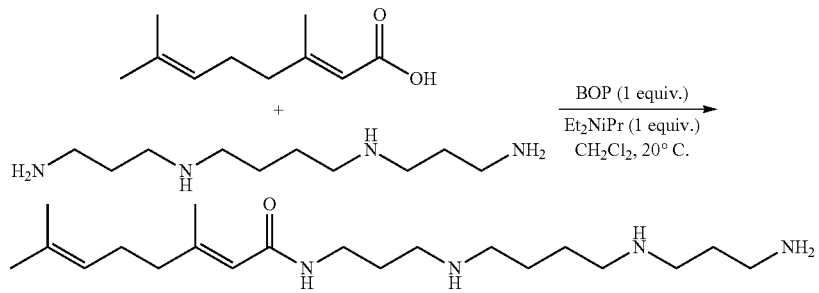

In a 50 mL two necked round flask were placed at room temperature under argon geranic acid (250 mg, 1.5 10$^{-3}$ mol) and spermine (303 mg, 1.5 10$^{-3}$ mol) in anhydrous $CH_2Cl_2$ (15 mL). The mixture was placed under stirring and diisopropylethylamine (200 μL, 1.5 10$^{-2}$ mol) was slowly added, followed by the addition of the coupling reagent (BOP) (780 μg, 1.5 10$^{-3}$ mol) dissolved in 5 mL of anhydrous $CH_2Cl_2$. The reaction was stirred for 12 hours at 20° C. After removal of the solvents, the crude residue was purified by chromatography on a silicagel column using $CH_2Cl_2$/MeOH/

Example 2

General Procedure for the Synthesis of the Compounds 8-23 According to the Invention The general synthetic pathway for the preparation of polyaminoisoprenyl derivatives 8-23 of the invention can be illustrated by the example below which represents the preparation of compound 10.

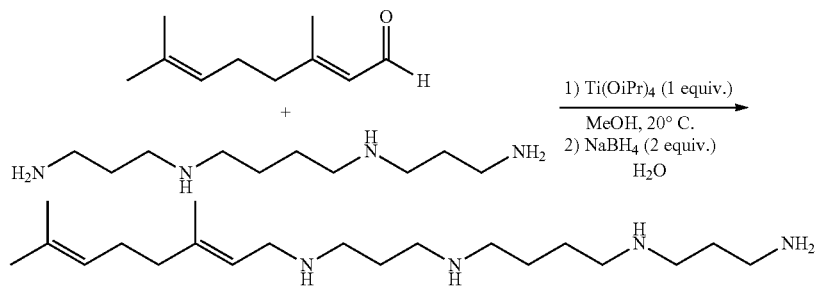

A mixture of citral (345 mg, 2.27 mmol), titanium(IV) isopropoxide (645 mg, 2.27 mmol) and spermine (2.27 mmol) in absolute methanol (5 mL) was stirred at room temperature for 12 hours. Sodium borohydride (172 mg, 4.5 mmol) was then added at 0° C. and the resulting mixture was stirred for an additional 2 hours. The reaction was then quenched by adding water (1 mL). Stirring was maintained at room temperature for 20 minutes. After filtration over a pad of Celite washing with methanol and ethylacetate, the solvents were removed under vaccuum and the crude amine was purified by flash chromatography on silicagel. using $CH_2Cl_2/MeOH/NH_4OH$ (7/3/1) as eluent affording the expected coupling product 10 in 64% yield.

Compound 10, Mixture of Z/E isomers, white solid; $^1H$ NMR (MeOD): δ=5.27-5.10 (m, 3H), 3.36-3.19 (m, 4H), 2.74-2.63 (m, 10H), 2.12-2.08 (m, 6H), 1.76-1.31 (m, 22H). $^{13}C$ (MeOD): δ=140.12, 133.18, 132.82, 125.60, 124.18, 123.30, 50.83, 48.38, 47.98, 47.94, 41.39, 41.22, 33.49, 30.40, 30.30, 28.56, 27.98, 27.95, 26.42, 26.38, 24.14, 18.24, 16.83. $C_{20}H_{42}N_4$ m/z 339.3482 (100%, (M+H$^+$))

Compound 8, Yellow solid; $^1H$ NMR (MeOD): δ=5.05-4.93 (m, 3H), 2.93-2.57 (m, 14H), 2.19-1.92 (m, 10H), 1.63-0.97 (m, 23H). $^{13}C$ (MeOD): δ=142.24, 134.83, 131.09, 124.86, 124.17, 117.32, 47.90, 47.69, 47.64, 46.61, 44.01, 40.60, 39.83, 33.97, 31.20, 26.97, 26.30, 25.66, 25.11, 24.90, 17.62, 16.90, 15.93.

Compound 9, Yellow solid; $^1H$ NMR (MeOD): δ=5.03-4.95 (m, 3H), 2.93-2.64 (m, 8H), 2.36-1.92 (m, 14H), 1.65-1.39 (m, 23H). $^{13}C$ (MeOD): δ=142.31, 134.93, 131.09, 124.76, 124.17, 117.39, 52.88, 51.68, 48.19, 44.00, 40.30, 39.33, 31.20, 30.98, 27.67, 26.93, 26.30, 25.66, 17.62, 16.90, 15.32.

Compound 11, Mixture of Z/E isomers, Yellow solid; $^1H$ NMR (MeOD): δ=5.28-5.10 (m, 3H), 3.34-3.19 (m, 4H), 2.76-2.53 (m, 9H), 2.12-2.09 (m, 6H), 1.77-1.63 (m, 20H). $^{13}C$ (MeOD): δ=140.95, 133.26, 132.91, 125.53, 123.42, 122.43, 53.51, 53.06, 48.73, 47.90, 47.64, 47.61, 41.22, 41.10, 33.53, 29.66, 27.94, 27.50, 27.37, 26.44, 26.40, 24.17, 18.25, 16.91. $C_{19}H_{40}N_4$ m/z 325.3326 (100%, (M+H$^+$)).

Compound 12, Yellow solid; $^1H$ NMR (MeOD): δ=5.05-4.93 (m, 2H), 2.93-2.78 (m, 4H), 2.18-1.92 (m, 5H), 1.63-1.18 (m, 15H). $^{13}C$ (MeOD): δ=136.20, 133.14, 124.83, 120.12, 47.18, 44.12, 40.60, 39.17, 33.14, 26.82, 25.38, 18.01, 17.84.

Compound 13, Yellow solid; $^1H$ NMR (MeOD): δ=5.04-4.97 (m, 2H), 2.91-2.75 (m, 5H), 2.18-1.97 (m, 7H), 1.67-1.08 (m, 22H). $^{13}C$ (MeOD): δ=136.77, 132.43, 125.41, 118.12, 55.84, 55.54, 44.12, 39.68, 39.37, 38.12, 30.60, 27.07, 26.62, 25.70, 17.18, 16.95, 14.15

Compound 14, Mixture of Z/E isomers, Yellow solid; $^1H$ NMR (MeOD): δ=5.29-5.14 (m, 4H), 3.34-3.31 (m, 3H), 2.79-2.63 (m, 4H), 2.48-2.45 (m, 4H), 2.26 (s, 3H), 2.14-1.93 (m, 8H), 1.77-1.63 (m, 18H). $^{13}C$ (MeOD): δ=136.67, 136.43, 136.32, 132.44, 132.22, 132.17, 125.86, 125.44, 125.40, 125.15, 125.00, 56.79, 56.40, 47.33, 42.24, 41.12, 40.93, 40.63, 33.07, 32.99, 28.93, 27.86, 27.76, 27.43, 26.07, 26.02, 23.80, 17.89, 16.58, 16.23.

Compound 15, Mixture of Z/E isomers, Yellow solid; $^1H$ NMR (MeOD): δ=5.09-4.92 (m, 3H), 2.91-2.61 (m, 6H), 2.56-2.48 (m, 4H), 2.08-1.98 (m, 6H), 1.67-1.46 (m, 21H). $^{13}C$ (MeOD): δ=140.11, 139.95, 137.89, 136.58, 132.58, 132.15, 125.99, 125.43, 125.17, 52.36, 52.03, 51.68, 51.56, 48.19, 43.82, 40.29, 39.77, 31.02, 27.34, 26.82, 26.78, 26.28, 25.89, 25.66, 24.32, 17.54, 16.90, 15.84

Compound 16, Mixture of Z/E isomers, Yellow solid; $^1H$ NMR (MeOD): δ=5.18-5.01 (m, 4H), 3.22-3.08 (m, 3H), 2.84-2.64 (m, 4H), 2.09-1.90 (m, 8H), 1.66-1.02 (m, 18H). $^{13}C$ (MeOD): δ=136.77, 136.64, 136.44, 136.33, 132.43, 132.17, 125.41, 125.37, 54.34, 47.25, 47.17, 41.33, 40.90, 40.80, 40.14, 32.95, 30.53, 28.86, 27.73, 27.77, 27.65, 27.42, 26.02, 25.97, 23.73, 17.82, 16.52, 16.25.

Compound 17, Mixture of Z/E isomers, Yellow solid; $^1H$ NMR (MeOD): δ=5.19-4.99 (m, 3H), 2.73-2.56 (m, 4H), 3.32-3.06 (m, 3H), 2.73-2.56 (m, 4H), 2.03-1.80 (m, 9H), 1.67-1.09 (m, 20H). $^{13}C$ (MeOD): δ=142.52, 142.41, 136.54, 136.42, 132.45, 132.24, 132.18, 125.73, 125.41, 125.37, 125.05, 121.15, 120.11, 120.02, 54.446, 46.88, 41.15, 40.90, 40.80, 33.38, 33.07, 32.96, 28.79, 28.73, 27.83, 27.41, 27.34, 26.05, 26.00, 24.39, 23.82, 23.76, 22.17, 17.86, 16.60, 16.19.

Compound 18, Mixture of Z/E isomers, Yellow solid; $^1H$ NMR (MeOD): δ=5.28-5.11 (m, 4H), 3.43-3.19 (m, 3H), 2.75-2.61 (m, 4H), 2.14-2.06 (m, 9H), 1.77-1.40 (m, 22H). $^{13}C$ 125.00, 121.92, 121.28, 47.39, 41.87, 40.89, 40.17, 33.03, 27.83, 27.76, 27.38, 25.94, 25.55, 23.73, 17.79, 16.45, 16.12.

Compound 19, Mixture of Z/E isomers, Yellow solid; $^1H$ NMR (MeOD): δ=5.17-4.99 (m, 3H), 3.22-3.15 (m, 4H), 2.67-2.54 (m, 7H), 2.02-1.90 (m, 10H), 1.65-1.16 (m, 26H). $^{13}C$ (MeOD): δ=141.12, 140.40, 136.62, 136.38, 132.48, 132.16, 125.83, 125.43, 125.39, 125.17, 47.44, 47.25, 41.84, 40.90, 40.80, 31.96, 28.84, 27.78, 27.44, 26.03, 25.99, 23.74, 17.84, 16.52, 16.17.

Compound 20, Mixture of Z/E isomers, Yellow solid; $^1H$ NMR (MeOD): δ=5.17-4.97 (m, 3H), 3.20-3.18 (m, 4H), 2.66-2.54 (m, 7H), 2.02-1.90 (m, 10H), 1.63-1.24 (m, 24H). $^{13}C$ (MeOD): δ=140.12, 140.00, 137.62, 136.68, 132.58, 132.26, 125.83, 125.43, 125.37, 125.07, 47.43, 47.28, 41.14, 40.90, 40.78, 31.96, 28.84, 27.78, 27.44, 26.03, 25.99, 22.74, 17.84, 16.57, 16.21.

Compound 21, Mixture of Z/E isomers, Yellow solid; $^1H$ NMR (MeOD): δ=5.15-4.95 (m, 2H), 2.97-2.68 (m, 6H), 2.50-2.48 (m, 4H), 2.09-1.98 (m, 4H), 1.68-1.48 (m, 17H), 0.95 (t, J=6 Hz, 6H). $^{13}$C (MeOD): δ=136.10, 136.04, 132.80, 124.05, 123.92, 117.32, 49.51, 47.93, 47.67, 47.30, 44.00, 40.78, 39.68, 26.62, 25.92, 25.70, 24.63, 17.80, 17.03, 16.90, 8.13.

Compound 22, Mixture of Z/E isomers, Yellow solid; $^1$H NMR (MeOD): δ=5.14-4.92 (m, 3H), 2.93-2.68 (m, 6H), 2.56-2.48 (m, 4H), 2.09-1.98 (m, 6H), 1.68-1.48 (m, 21H). $^{13}$C (MeOD): δ=140.12, 140.00, 136.10, 136.01, 124.03, 123.92, 117.42, 54.70, 51.38, 48.19, 43.27, 39.72, 31.40, 27.50, 26.34, 25.42, 25.34, 25.20, 23.56, 17.62, 16.83, 15.18.

Compound 23, Mixture of Z/E isomers, Yellow solid; $^1$H NMR (MeOD): δ=5.09-4.92 (m, 3H), 2.91-2.61 (m, 6H), 2.56-2.48 (m, 4H), 2.08-1.98 (m, 6H), 1.67-1.46 (m, 21H). $^{13}$C (MeOD): δ=140.14, 139.86, 137.61, 136.68, 132.48, 132.25, 125.83, 125.43, 125.32, 66.70, 66.32, 53.73, 51.92, 48.19, 44.00, 39.37, 31.20, 27.49, 26.82, 26.30, 25.66, 17.62, 16.90, 15.84.

Example 3

Activities of the Compounds According to the Invention

Materials and Methods

The process consists of treating the MDR bacteria with the compounds of the invention in the presence of antibiotics. A compound is considered active once it has induced increased activity of an antibiotic, which we have quantified as MIC ratio in table 2 of this description. This increase in efficiency is observed when the dose of antibiotic required to kill a MDR bacterium is at least 8 times smaller than it would be without the compound of the invention.

Bacterial Strains Used in this Study

The *Enterobacter aerogenes* Ea289 strain is a Kan$^s$ derivative of the MDR clinical isolate Ea27, the acrB mutant, EaEP294, was constructed from Ea289. Multidrug-resistant *Salmonella enterica* serovar Typhimurium DT104 strains (BN10055) was isolated from cattle in France, the isogenic acrB derivative mutant, BN10055ΔacrB, was constructed from BN10055. Strains were maintained at −80° C. in 25% (v/v) glycerol for cryoprotection. Bacteria were routinely grown in Mueller-Hinton (MH) broth at 37° C.

| Bacterial strains | Relevant features | Chl-MIC | References |
|---|---|---|---|
| *E. aerogenes* strains | | | |
| Ea289 | Kan$^s$ derivative of Ea27 | 1024 | 1 |
| Ea294 | Ea289 acrA::Kan$^r$ | 64 | 1 |
| *S. enterica* Typhimurium strains | | | |
| BN10055 | MDR clinical isolate, Kan$^s$ | 256 | 11 |
| BN10055ΔacrB | BN10055 ΔacrB::Kan$^r$ | 16 | 11 |

Amp$^r$, Chl$^r$, Kan$^r$, Nal$^r$, Str$^r$, and Tet$^r$, resistance to ampicillin, chloramphenicol, kanamycin, nalidixic acid, streptomycin, and tetracycline, respectively
Chl-MIC: Chloramphenicol (mg/l) Minimal Inhibitory Concentration Antibiotics Nalidixic acid, doxycycline, erythromycin and chloramphenicol were purchased from Sigma (St Quentin Fallavier, France). They were dissolved in water, in ethanol or in DMSO depending on their solubility. It was established that ethanol concentration up to 5% v/v and a DMSO concentration up to 2.5% had no detrimental effect on bacterial growth.

Antibiotic Susceptibility Testing

Susceptibilities to antibiotics and compounds were determined in microplates by broth dilution method, as previously described. Minimal Inhibitory Concentrations (MICs) were determined with an inoculum of 106 CFU in 200 μL of MH broth containing two-fold serial dilutions of each drug. The MIC was defined as the lowest concentration of drug that completely inhibited visible growth after incubation for 18 h at 37° C. All MIC determinations were repeated at least three times in independent experiments.

Determination of MICs of Antibiotics±Synergizing Compounds

The MICs of chloramphenicol±test compounds (MIC/4) were determined by the micro-broth dilution method (9). All MIC determinations were repeated at least three times in independent experiments. The MIC ratio corresponds to the ratio of the MIC of an antibiotic alone to the MIC of the same antibiotic in the presence of the tested compound (at MIC/4).

Two sets of experiments were performed:
  Set 1—The compounds 1-11 of table 1 were assayed on 4 strains, the *Enterobacter aerogenes* MDR Ea289 and its isogenic acrAB mutant (1), the *Salmonella Thyphimurium* MDR BN10055 and its isogenic acrAB mutant (11). Their synergistic activities at MIC/4 with three antibiotics (chloramphenicol, erythromycin and nalidixic acid) were analyzed
  Set 2—The compounds 1-40 shown in table 1 were assayed on the same strains as in set of experiments 1 so as to assay their synergistic activity at MIC/4 with chloramphenicol, doxocycline and nalidixic acid.

Toxicity of Compounds:

The toxicity of each compound was determined on CHO cultured cells. Incubation of CHO cells was performed with serial dilution of compounds. The compounds are either solubilized in DMSO or in PBS. The IC50 of some compounds are shown in Table 2. The IC50 corresponds to the concentration of compounds leading to a killing of 50% of the CHO cells after 24 hours of incubation.

Results

Toxicity of the Compounds

The IC50 of some compounds according to the invention are shown in table 2. The majority of the compounds showed in table 1 had a IC50 higher than 100 μM. Noteworthy, compounds of table 1 for which n=1 displayed higher a IC50 than compounds for which n=2.

Intrinsic Activity of Compounds:

Determination of the minimal inhibitory concentration (MIC) of each compound was a prerequisite to further analyse their synergistic behaviour with antibiotics at a concentration below their intrinsic activity. The MIC's showed great variations depending on the identity of the compound and the strains.

Synergistic Activity of the Compounds with Chloramphenicol:

The compounds listed in Table 2 were tested for their ability to decrease the chloramphenicol MIC of Ea289, an *Enterobacter aerogenes* MDR strain (1). Each compound was first tested at MIC/4. When the MIC ratio of chloramphenicol reached a value over 8, the concentration of the compound was further decreased in order to reach a concentration leading to a MIC ratio of 8. All MIC determinations were repeated at least three times in independent experiments. The results show that compounds 5, 7, 8, 9, 10 and 11 exhibited a strong activity with a similar or lower effective concentration than PAβN to reach a MIC ratio of 8. Moreover compounds 8, 9, 10 and 11 exhibited an efficient concentration that is about 4.9 times lower than the control PAβN. In addition, the IC50 for these compounds on CHO cells are far higher their effective concentrations. The higher difference was observed with compound 10, its IC50 is about 300 times higher than its effective concentration (Table 2).

TABLE 2

Effective concentration of compounds

| Name | Molar Mass (g/Mole) | IC50 (mM) on CHO Cells | Effective concentration (mM) for a MIC ratio of chloramphenicol ≥ 8 on Ea289 |
|---|---|---|---|
| PAβN | 519.47 | >5 | 0.038 |
| compound 1 | 205 | >0.15 | >2.5 |
| compound 2 | 236 | >0.15 | 0.25 |
| compound 3 | 180 | 0.12 | 0.25 |
| compound 4 | 195 | >0.15 | >0.25 |
| compound 5 | 231 | 0.29 | 0.0625 |
| compound 6 | 250 | 0.14 | >0.25 |
| compound 7 | 252 | >0.15 | 0.020 |
| compound 8 | 292 | 0.726 | 0.0078 |
| compound 9 | 278 | 0.132 | 0.0078 |
| compound 10 | 238 | 2.33 | 0.0078 |
| compound 11 | 224 | 0.282 | 0.0078 |

Synergistic Activity of the Compounds with Chloramphenicol, Macrolides, Quinolones and Tetracyclines:

Set 1 of Experiments

The compounds were assayed on 4 strains, the *Enterobacter aerogenes* MDR Ea289 and its isogenic acrAB mutant (1), the *Salmonella Thyphimurium* MDR BN10055 and its isogenic acrAB mutant (11). Their synergistic activities at MIC/4 with three antibiotics were analyzed, chloramphenicol, erythromycin and nalidixic acid (Table 3).

A significant MIC ratio was observed for each compound in association with either chloramphenicol (Chl), erythromycin (Ery) or nalidixic acid (Nal) on the 4 strains tested except for compound 1. The higher MIC ratios were obtained on the two MDR strains compared to their isogenic acrAB mutants suggesting a strong efficiency of our compounds on the efflux pump AcrAB-TolC. There are 6 compounds (compounds 5, 7, 8, 9, 10, and 11) that gave a MIC ratio≥16 for at least two antibiotics on the two MDR strains. In addition, compounds 8 and 9 gave a MIC ratio≥16 on Ea289 for the three antibiotics tested. Similarly compounds 5 and 9 gave a MIC ratio≥16 for the three antibiotics tested on the strain BN10005. Taking together, these results demonstrated that several compounds exhibited a synergistic activity with antibiotics on gram negative MDR strains and that compound 9 is one of the most active compound already tested.

TABLE 3

Synergistic activity of compounds on MDR strains and isogenic mutants

| | MIC ratio (*) on Ea289 | | | MIC ratio (*) on Ea289ΔacrB | | | MIC ratio (*) on BN10055 | | | MIC ratio (*) on BN10055ΔacrB | | |
|---|---|---|---|---|---|---|---|---|---|---|---|---|
| Compound | Chl | Ery | Nal | Chl | Ery | Nal | Chl | Ery | Nal | Chl | Ery | Nal |
| compound 1 | 2 | 1 | 1 | 2 | 1 | 1 | 1 | 1 | 1 | 2 | 1 | 1 |
| compound 2 | 8 | 32 | 4 | 2 | 16 | 2 | 8 | 32 | 64 | 4 | 4 | 2 |
| compound 3 | 8 | 32 | 8 | 1 | 4 | 2 | 4 | 16 | 64 | 4 | 4 | 2 |
| compound 4 | 4 | 4 | 2 | 1 | 4 | 2 | 2 | 1 | 64 | 4 | 1 | 2 |
| compound 5 | 8 | 16 | >8 | 2 | 2 | 2 | >16 | 64 | 64 | 2 | 16 | 4 |
| compound 6 | 2 | 2 | 1 | 1 | 1 | 2 | 2 | 2 | 4 | 2 | 1 | 1 |
| compound 7 | 16 | 16 | 4 | 8 | 8 | 4 | 8 | 16 | 32 | 2 | 8 | 2 |
| compound 8 | 8-16 | 32 | >16 | 2 | 16 | 4 | >16 | 8 | 64 | 4 | 8 | 4 |
| compound 9 | 32 | 16-32 | 16 | 4 | 8 | 128 | 16 | 32 | 128 | 2 | 8 | 8 |
| compound 10 | 16 | 4 | 16 | 16 | 8 | 8 | 16 | 4 | 64 | 2 | 8 | 2 |
| compound 11 | 16 | 32 | 8 | 16 | 16 | 8 | 16 | 8 | 128 | 2 | 8 | 2 |

(*) The MIC ratio corresponds to the ratio of the MIC of an antibiotic alone to the MIC of the same antibiotic in the presence of the tested compound (at MIC/4).

Set 2 of Experiments

Most of the tested compounds were able to reduce the resistant to at least one antibiotic in the MDR strain Ea289 and/or in the MDR strain BN10055.

Table 4 hereunder shows the compounds of table 1 for which MIC ratios≥8 were obtained for chloramphenicol, doxycycline and nalidixic acid in both MDR strains Ea289 and BN10055. These compounds are particularly interesting for reducing resistance or restoring susceptibility to antibiotics in gram-negative strains, for example in *Enterobacter* and *Salmonella* MDR strains.

TABLE 4

Synergistic activity of compounds of the invention with chloramphenicol (Chl), doxycycline (Dox) and nalidixic acid (Nal)

| | MIC ratio (*) on Ea289 | | | MIC ratio (*) on BN10055 | | |
|---|---|---|---|---|---|---|
| | Chl | Dox | Nal | Chl | Dox | Nal |
| Compound 5 | 8 | 16 | 8-16 | 16 | 16 | 64 |
| Compound 8 | 8-16 | 16 | 16-32 | 16-32 | 8 | 64 |
| Compound 9 | 32 | 16 | 16 | 16 | 8 | 128 |
| Compound 10 | 8 | 16 | 16 | 16 | 16 | 64 |
| Compound 11 | 8 | 32 | 8 | 16 | 16 | 128 |
| Compound 12 | 16 | 16 | 4-8 | 8 | 16 | 32 |
| Compound 13 | 16 | 16 | 8 | 8-16 | 16 | 32 |
| Compound 14 | 8 | 64 | 32 | 16 | 64 | 128 |
| Compound 15 | 8 | 128 | 32 | 8 | 32 | 64 |
| Compound 16 | 8-16 | 64 | 16 | 16-32 | 32 | 128 |
| Compound 17 | 8-16 | 64 | 16 | 8 | 16 | 64 |
| Compound 18 | 8-16 | 64 | 8 | 4-8 | 16 | 16 |
| Compound 19 | 8-16 | 64 | 16 | 8-16 | 16 | 64 |
| Compound 20 | 8 | 32 | 8 | 8 | 32 | 64 |
| Compound 21 | 8-16 | 32 | 8 | 16 | 32 | 64 |
| Compound 22 | 8-16 | 32 | 16 | 16 | 32 | 128 |
| Compound 23 | 8 | 32 | 8 | 8 | 16 | 32 |

(*) The MIC ratio corresponds to the ratio of the MIC of an antibiotic alone to the MIC of the same antibiotic in the presence of the tested compound (at MIC/4).

It should be further noticed that compounds 8, 11, 12, 13, 14, 15, 36, 16, 17, 18, 19, 20, 21, 22 and 23 significantly reduced the MDR resistant of Ea289 to chloramphenicol, doxycycline, nalidixic acid and erythromycin since the MIC ratios for all these antibiotics were higher or equal to 8. These compounds may be useful for increasing the susceptibility of *Enterobacter* strains to antibiotics.

Compounds 14, 15, 37, 16 and 17 induced a MIC ratio≥128 in Ea289 strain for erythromycin. These compounds may be advantageously used for increasing sensitivity to macrolides in *Enterobacter* MDR strains.

In the case of BN100555 strains, the MICs>8 for erythromycin were also obtained for compounds 14, 37, 16 and 22.

Finally, it should be also noticed that compound 35 also reduced the resistance of both Ea289 and BN100055 for doxycycline and nalidixic acid (MICs>8).

Example 4

Further Assays Concerning Compound 11 and Compound 14

The ability of compounds 11 and 14 for reducing drug resistance in various strains of Gram-negative bacteria was assessed.

TABLE 5

Strains and antibiotics assessed in Example 4

| Bacteria species | Strains | Features and Reference | Antibiotics |
|---|---|---|---|
| *Enterobacter aerogenes* | Ea289 | Ref 6 | Chloramphenicol |
| | Ea294 | Ref 6 | Nalidixic acid |
| | Ea27 | Ref 7 et 8 | Doxycycline |
| | ATCC 13048 | Rf 7 et 8 | Oxacillin |
| | | Reference strain | |
| | CM64 | Ref 7 et 8 | |
| *Salmonella enterica* | BN10055 | Ref 11 | |
| | BN10055ΔacrB | Ref 11 | |
| *Escherichia coli* | AG100 | Ref 6 | |
| | | Reference strain | |
| *Pseudomonas aeruginosa* | PAO1 | Ref 6 | Chloramphenicol |
| | | Reference strain | Doxycycline |
| | PA124 | Ref 6 | Cefepime |
| *Acinetobacter baumannii* | ATCC 19606 | Ref 12 | Tetracycline |
| | | Reference strain | |
| | AB1 | Ref 12 | |

The activity of compounds 11 and 14 i.e. their ability to reduce antibiotic resistance and/or increase antibiotic sensitivity was assessed as described in Example 3 by determining the MIC ratios. For reminder, the MIC ratio corresponds to the ratio of the MIC of the assessed antibiotic alone to the MIC of the same antibiotic in the presence of the tested compound (at MIC/4).

In a first step, the intrinsic MIC of compounds 11 and 14 for each strain was determined. In a second step, the MIC of each antibiotic for each strain was assessed in the absence of the test compound or in the presence of the test compound at a concentration equal to 0.25-fold its intrinsic MIC (MIC/4).

The intrinsic MICs of compounds 11 and 14 are shown in Table 6. The MICs for compounds 11 and 14 are slightly higher for *Pseudomonas* and *Acinetobacter*.

TABLE 6 intrinsic MIC of compound 11 and compound 14 for each assessed strain.

| | Strains | MIC for Compound 11 (μM) | Compound 14 (μM) |
|---|---|---|---|
| *Enterobacter* | Ea289 | 31 | 31 |
| | Ea294 | 15 | 15 |
| | Ea27 | 31 | 31 |
| | ATCC 13048 | 31 | 31 |
| | CM64 | 31 | 31 |
| *Salmonella* | BN10055 | 31 | 31 |
| | BN10055ΔacrB | 15 | 15 |
| *Escherichia coli* | AG100 | 31 | 62 |
| *Pseudomonas* | PAO1 | 62 | 250 |
| | PA124 | 62 | 250 |
| *Acinetobacter* | ATCC 19606 | 62 | 62 |
| | AB1 | 31 | 62 |

As shown in below table 7, Compounds 4 and 11 increased the sensitivity of *Enterobacter Salmonella* and *Escherichia* strains for chloramphenicol, nalidixic acid, doxycycline and oxacillin. Such a result illustrates that the activity of the compounds of the invention is not limited to a specific strain nor to a specific antibiotic. Notably, the synergic effect is not only restricted to MDR strains, namely strains which have developed mechanisms to circumvent the action of antibiotics.

Compounds 4 and 11 were also able to increase antibiotic sensibility of *Pseudomonas* and *Actinebacter* strains which are known to be more resistant (see table 8). Compounds 4 and 11 greatly increased the sensitivity of strains to chloramphenicol. Noteworthy, compounds 4 and 11 increased the sensitivity of *Pseudomonas* and *Actinebacter* strains to tetracycline whereas such an increase was not observed for *Enterobacter, Salmonella* and *E. coli* strains (data not shown).

TABLE 7

MIC ratios for compounds 11 and 14 obtained for *Enterobacter*, *Salmonella* and *Escherichia* strains

| | | MIC ratio | | | | | | | |
|---|---|---|---|---|---|---|---|---|---|
| | Compound | E. aerogenes | | | | | S. enterica | | E. Coli |
| Antibiotics | Number | Ea289 | Ea294 | Ea27 | ATCC13048 | CM64 | BN10055 | BN1005ΔacrB | AG100 |
| Chloramphenicol | 11 | 8 | 16 | >4 | >32 | 16 | 16 | 2 | 16 |
| | 14 | 8 | 2 | >4 | >32 | 16 | 16 | 2 | 16 |
| Nalidixic acid | 11 | 8 | 8 | n.d | n.d | n.d | 128 | 2 | n.d |
| | 14 | 32 | 4 | n.d | n.d | n.d | 128 | 4 | n.d |
| Doxycycline | 11 | 32 | 4 | 32 | 64 | n.d | 16 | 2 | >32 |
| | 14 | 64 | 4 | 32 | 64 | n.d | 64 | 2 | >32 |
| Oxacillin | 11 | n.d | n.d | 1 | >8 | >8 | n.d | n.d | 16 |
| | 14 | n.d | n.d | 1 | >8 | >8 | n.d | n.d | 16 |

TABLE 8

MIC ratios for compounds 11 and 14 obtained for
*Pseudomonas* and *Acitenobacter* strains

| | | *Pseudomonas aeruginosa* | | *Acinetobacter baumannii* | |
| --- | --- | --- | --- | --- | --- |
| Nom de l'ATB | Compound Number | PAO1 | PA124 | ATCC19606 | AB1 |
| Chloramphénicol | 11 | n.d | 128 | 8 | 16 |
|  | 14 | n.d | 128 | 8 | 16 |
| Doxycycline | 11 | >16 | >32 | 1 | 2 |
|  | 14 | >16 | >32 | 1 | 2 |
| Cefepime | 11 | 1 | 1 | 4-8 | 1 |
|  | 14 | 1 | 1 | 4-8 | 1 |
| Tetracycline | 11 | n.d | 8 | 8 | 2 |
|  | 14 | n.d | 8 | 4 | 4 | n.d: not determined (no assay) - The MIC ratio corresponds to the ratio of the MIC of an antibiotic alone to the MIC of the same antibiotic in the presence of the tested compound (at MIC/4).

Example 5

The Compounds of the Invention Decrease MIC of Macrolide Antibiotics in Various Gram-Negative Strains The compounds of the invention may be also effective for making gram-negative strains, such as *Enterobacter, Salmonella, E. coli, Pseudomonas* or *Acinetobacter* strains, sensible to macrolide antibiotics. Such a result is quite surprising since gram-negative bacteria are known to be naturally resistant to macrolides.

Example 3 shows that various compounds of the invention were able to reduce MIC for erythromycin in *Salmonella* and *Enterobacter* strains.

For confirming this result, the MICs of erythromycin, spiramycin and clarithromycin in several gram-negative strains were assessed in the presence of test compounds 7, 2, 3 or 4 as described in Example 3. PAβN was used as positive control.

The results are shown in the table 9 hereunder. Compounds 7, 3 and 4 were able to increase the sensibility of the strains to at least one macrolide drugs. Notably, in the presence of compound 7, the four distinct strains became susceptible to erythromycin, clarithromycin and spiramycin.

Example 6

Genotoxicity and Drug Tolerance a. Micronucleus Assay

Material and Methods:

Genotoxicity of compounds 11 and 14 was assessed by micronucleus test. The micronucleus test was performed on CHO-K1 cells with and without metabolic activation. Metabolic activation is obtained by adding in the medium S9 mix. S9 mix contains NADP, G6P and S9 fraction which is a crude preparation of enzymes obtained from the homogenized liver of rats. Briefly, CHO-K1 cells were cultured in Mc Coy's medium 5A and then transferred in the wells of Lab-Tek chamber slides at a concentration of 100 000 cells/ml. The cells were incubated during 24 h at 37° C. at $CO_2$ (5%). The culture medium was replaced by Mc Coy's 5A medium comprising 10% per volume of S9 mix. The test compounds were added at increased concentrations. After being incubated during three hours at 37° C., the cells were rinsed with phosphate buffer (PBS) and then cultured in Mac Coy's 5A medium containing 3 µg/ml cytochalasine B. After an incubation of 21 hours at 37° C., the cells were rinsed, fixed with methanol and coloured with Giemsa 10% during 20 minutes. For each set of assays, the positive control was 0.05 µg/ml of mitomycine C or 5 µg/ml of benzo-a-pyrene. The negative control was culture medium containing 5% of PBS. The stained cells were then analysed by microscopy for the presence of micronuclei. The proliferation index was determined as follows: IP=(2×BIN+MON)/500. MON: number of mononucleated cells and BIN: number of binucleated cells.

Results:

Compound 14 was tested at concentrations ranging from 1.5 µM to 30 µM with and without S9 mix. Proliferation index for compound 14 ranged from 99.7% to 58.4% depending on its concentration in cell medium.

Compound 11 was tested at concentrations ranging from 50 µM to 1 mM in the absence of S9 mix and at concentrations from 5 nM to 0.1 µM with S9 mix. Proliferation index ranged from 96% to 52% depending on the tested concentration.

For all the tested concentrations, Compounds 11 and 14 had thus a proliferation index higher than 50% which showed that the said compounds were not genotoxic in vitro.

TABLE 9

Susceptibility of Gram-negative strains to macrolides.
++ means that the strain is susceptible, + means that the strain is partially susceptible,
− means that the strain is poorly susceptible

| Antibiotics | N° compound | *A. Baumannii* ATCC19606 | *E. Coli* AG100 | *E. aerogenes* ATCC13048 | *S. enterica* Thyphimurium ATCC13311 |
| --- | --- | --- | --- | --- | --- |
| Erythromycin | PAβN | + | ++ | + | ++ |
|  | Compound 7 | + | ++ | ++ | ++ |
|  | Compound 3 | + | ++ | + | ++ |
|  | Compound 4 | + | + | − | + |
| Clarithomycin | PAβN | ++ | ++ | + | ++ |
|  | Compound 7 | ++ | ++ | ++ | ++ |
|  | Compound 3 | ++ | ++ | + | ++ |
|  | Compound 4 | + | ++ | − | ++ |
| Spiramycin | PAβN | + | + | + | ++ |
|  | Compound 7 | + | + | ++ | ++ |
|  | Compound 3 | + | + | ++ | ++ |
|  | Compound 4 | − | + | + | + |
|  | Compound 2 | + | + | − | ++ | b. Tolerance of the Compounds of the Invention

Mice were administered with increasing doses of test compounds by intraperitoneal route. The mice were sacrificed on day 2 after the injection of the test compound and autopsied. No morphological anomaly was observed. Liver, lung, kidney and intestine of each mouse were fixed and analysed. For all the assessed compounds—namely Compound 5 (8.8 mg/kg), Compound 8 (1.46 mg/kg), Compound 11 (0.45 mg/kg), Compound 14 (0.35 mg/kg) and Compound 12 (6.3 mg/kg)—no significant tissue anomaly was recorded.

However, for the highest dose of compound 5—namely 35.25 mg/kg—slight vascular modifications were observed which suggests that compound 5 may have a slight anticoagulant effect at high dose.

Examples 7

Veterinary Uses of the Compounds According to the Invention

The compounds of the invention may be useful for treating or preventing bacterial diseases in humans but also in animals by increasing antibiotic-susceptibility, in particular susceptibility to macrolides.

The efficiency of compounds 7, 5, 10, 11, 14, 15 and 35 was assessed as described above (see e.g. example 3) for the following antibiotics and bacterial strains which infect animals:

TABLE 10 strains and antibiotics

| Species | Strain | Antibiotics |
|---|---|---|
| Escherichia coli pig | IV2571223 sensible | Tylosine |
| | IV2571418 resistant | Doxycycline |
| Escherichia coli cattle | IV2570060 sensible | |
| | IV2570533 resistant | |

For each strain and each antibiotic, the MICs were determined in the presence and in the absence of one test compound. The results are shown in tables below:

TABLE 11

MIC for strain IV2571223 - Escherichia coli pig

| N° compound | Concentration (μM) | Tylosine | Doxycycline |
|---|---|---|---|
| | No compound | 256 | 1 |
| 7 | 50 | 4 | 0.03125 |
| 5 | 50 | 2 | 0.0625 |
| 10 | 30 | 4 | 0.0625 |
| 11 | 2 | 16 | 0.03125 |
| 14 | 4 | 2 | 0.03125 |
| 15 | 4 | 32 | 0.0625 |
| 35 | 2 | 32 | 0.0625 |

TABLE 12

MIC for strain IV2571418- Escherichia coli pig

| N° compound | Concentration (μM) | Tylosine | Doxycycline |
|---|---|---|---|
| | No compound | 256 | 16 |
| 7 | 50 | 8 | 2 |
| 5 | 50 | 8 | 4 |
| 10 | 30 | 16 | 2 |
| 11 | 4 | 4 | 2 |
| 14 | 4 | 4 | 2 |
| 15 | 7 | 32 | 4 |
| 35 | 4 | 8 | 2 |

TABLE 13

MIC for strain IV2570060 - Escherichia coli cattle

| N° compound | Concentration (μM) | Tylosine | Doxycycline |
|---|---|---|---|
| | No compound | >256 | 1 |
| 7 | 50 | 4 | 0.125 |
| 5 | 50 | 8 | 0.125 |
| 10 | 30 | 16 | 0.125 |
| 11 | 4 | 4 | 0.0625 |
| 14 | 4 | 8 | 0.0625 |
| 15 | 7 | 32 | 0.125 |
| 35 | 4 | 8 | 0.0625 |

TABLE 14

MIC for strain IV2570533 - Escherichia coli cattle

| N° compound | Concentration (μM) | Tylosine | Doxycycline |
|---|---|---|---|
| | No compound | >256 | 8 |
| 7 | 12.6 | 4 | 2 |
| 5 | 11.55 | 4 | 2 |
| 10 | 7.14 | 8 | 2 |
| 11 | 0.896 | 4 | 1 |
| 14 | 1.396 | 8 | 1 |
| 15 | 2.828 | 32 | 2 |
| 35 | 1.744 | 4 | 1 |

All the tested compounds induced a significant decrease of MICs for tylosine and doxycycline in *E. coli* strains.

REFERENCES

1. Pradel E and Pagès J M. The AcrAB-TolC efflux pump contributes to multidrug resistance in the noscomial pathogen *Enterobacter aerogenes*. *J. Antimicrob. Chemother.* 2002 August; 46, (8):2640-3
2. Chollet R et al. RamA is an alternate activator of the multidrug resistance cascade in *Enterobacter aerogenes*. *J. Antimicrob. Chemother.* 2004 July; 48, (7):2518-23.
3. Chollet R et al. The AcrAB-TolC pump is involved in macrolide resistance but not in telithromycin efflux in *Enterobacter aerogenes* and *Escherichia coli*. *J. Antimicrob. Chemother.* 2004 September; 48, (9):3621-4
4. Mamelli L et al. Prevalence of efflux activity in low-level macrolide resistant *campylobacter* species. *J. Antimicrob. Chemother.* 2007 February; 59, (2):327-8
5. Chevalier J et al. Identification and evolution of an efflux pump in clinical *Enterobacter aerogenes* strains isolated in 1995 and 2003. *PloS One.* 2008 Sep. 12; 3(9):e3203.
6. Lorenzi V et al. Geraniol restores antibiotic activities against multidrug-resistant isolates from gram-negative species. *J. Antimicrob. Chemother.* 2009 May; 53, (5): 2209-11.
7. Ghisalberti D et al. Chloroquinolines block antibiotic efflux pumps in antibiotic-resistant *Enterobacter aerogenes* isolates. *Int J Antimicrob Agents.* 2006 June; 27(6): 565-9.

8. Chevalier J et al. Inhibitors of antibiotic efflux in resistant *Enterobacter aerogenes* and *Klebsiella pneumoniae* strains. *J. Antimicrob. Chemother.* 2004 March; 48, (3): 1043-6.

9. Malléa M et al. Alkylaminoquinolines inhibit the bacterial antibiotic efflux pump in multidrug resistant clinical isolates. *Biochem J* 2003 Dec. 15; 376(Pt 3):801-5.

10. Lorenzi V, Muselli A, Bernardini A F, Berti L, Pagès J M, Amaral L, Bolla J M. Geraniol restores antibiotic activities against multidrug-resistant isolates from Gram-negative species. Antimicrob Agents Chemother. 2009. 53, 2209-2211.

11. Baucheron S. et al., AcrAB-TolC directs efflux-mediated multidrug resistance in *Salmonella enterica* serovar Typhymurium DT104. Antimicrob Agents Chemother. 2004 48, 3729-3735.

12. Dupont M, Pagès J M, Lafitte D, Siroy A, Bollet C. Identification of an OprD homologue in *Acinetobacter baumannii*. J Proteome Res. 2005 November-December; 4(6):2386-90.

The invention claimed is:

1. A method for reducing antibiotic or antiseptic resistance or restoring antibiotic or antiseptic sensitivity to an antibiotic- or antiseptic-resistant bacterial strain in a subject, which method comprises administering to the subject an effective amount of one or more compounds of general formula (I):

wherein:
R represents an alkyl group, straight or branched, wherein said alkyl group is interrupted and/or terminated by at least one group selected from N, NH, $NH_2$, O, and S,
X represents a methylene group or a carbonyl group, and
A- represents a group of formula (II):

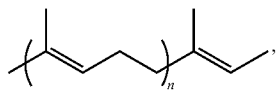

wherein:
n is an integer from 1 to 4.

2. The method according to claim 1, wherein the compound is used in combination with an antibiotic or an antiseptic.

3. The method according to claim 2, wherein the antibiotic is selected from the group consisting of beta-lactam antibiotics, macrolides, ketolides, monobactams, penicillins, cephalosporins, carbapenems, aminosides, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, tigecycline, bacitracin, quinolones, fluoroquinolones, glycopeptides, vancomycin, sulfamides and trimethoprim.

4. The method according to claim 1, wherein the subject is infected with an antibiotic-resistant bacterial strain or an antiseptic-resistant bacterial strain.

5. The method according to of claim 1, wherein the subject is an animal.

6. The method according to claim 1, wherein the bacterial strain is a Gram-negative bacterial strain.

7. The method according to claim 1, wherein the subject is infected with an enteropathogenic or uropathogenic bacterial strain.

8. The method according to claim 1, wherein the subject is infected with bacteria selected from the group consisting of *Enterobacter, Escherichia coli, Pseudomonas, Acinetobacter, Klebsellia, Salmonella, Burkholderia, Campylobacter* and *Helicobacter* species.

9. The method according to claim 1, wherein R is terminated by at least one $NH_2$ group.

10. The method according to claim 1, wherein R is interrupted and/or terminated by at least two groups selected from N, NH and $NH_2$.

11. The method according to claim 1, wherein n is 1 or 2.

12. The method of claim 11, wherein n is 1.

13. The method according to claim 1, wherein the compound is selected from the group consisting of:
3,7-Dimethyl-octa-2,6-dienoic acid {3-[bis-(3-amino-propyl)-amino]-propyl}-amide,
{3-[4-(3-Amino-propylamino)-butylamino]-propyl}-(3,7,11-trimethyl-dodeca-2,6,10-trienyl)-amine,
{3-[Bis-(3-amino-propyl)-amino]-propyl}-(3,7,11-trimethyl-dodeca-2,6,10-trienyl)-amine,
{3-[4-(3-Amino-propylamino)-butylamino]-propyl}-(3,7-dimethyl-octa-2,6-dienyl)-amine,
{3-[Bis-(3-amino-propyl)-amino]-propyl}-(3,7-dimethyl-octa-2,6-dienyl)-amine,
(3,7-Dimethyl-octa-2,6-dienyl)-propane-1,3-diamine,
{3-[(3-Amino-propyl)-methyl-amino]-propyl}-((E)-3,7-dimethyl-octa-2,6-dienyl)-amine,
{3-[(3-Amino-propyl)-methyl-amino]-propyl}-((2E,6E)-3,7,11-trimethyl-dodeca-2,6,10-trienyl)-amine,
{3-[4-(3-Amino-propyl)-piperazin-1-yl]-propyl}-((2E,6E)-3,7,11-trimethyl-dodeca-2,6,10-trienyl)-amine,
3,7,11-Trimethyl-dodeca-2,6,10-trienyl)-propane-1,3-diamine,
3,7,11-Trimethyl-dodeca-2,6,10-trienyl)-butane-1,4-diamine,
3,7,11-Trimethyl-dodeca-2,6,10-trienyl)-pentane-1,5-diamine,
[3-(4-Amino-butylamino)-propyl]-3,7,11-trimethyl-dodeca-2,6,10-trienyl)-amine,
[3-(3-Amino-propylamino)-propyl]-3,7,11-trimethyl-dodeca-2,6,10-trienyl)-amine,
[3-(2-Diethylamino-ethylamino)-propyl]-3,7-dimethyl-octa-2,6-dienyl)-amine,
(3-Pyrrolidin-1-yl-propyl)-3,7,11-trimethyl-dodeca-2,6,10-trienyl)-amine, and
(3-Morpholin-4-yl-propyl)-3,7,11-trimethyl-dodeca-2,6,10-trienyl)-amine.

14. The method of claim 1, wherein the compound of formula (I) is used in combination with an antibiotic or antiseptic agent, the effective dose of the antibiotic or antiseptic agent required to treat a bacterial infection in the subject is smaller when used in combination with a compound of formula (I) than the effective dose required without the compound of formula (I).

15. The method of claim 14, wherein the effective dose of the antibiotic or antiseptic agent required to treat a bacterial infection in the subject is at least about 8 times smaller when used in combination with a compound of formula (I) than the effective dose required without the compound of formula (I).

16. The method of claim 1, wherein the compound of formula (I) is used in combination with an antibiotic or antiseptic agent, the minimal inhibitory concentration of the antibiotic or antiseptic agent against a bacteria is decreased when used in combination with a compound of formula (I) compared to the minimal inhibitory concentration of the antibiotic or antiseptic agent without the compound of formula (I).

* * * * *